US012662519B2

(12) United States Patent
Aramini et al.

(10) Patent No.: US 12,662,519 B2
(45) Date of Patent: Jun. 23, 2026

(54) NERVE GROWTH FACTOR AND METHODS OF USE THEREOF FOR NEURODEVELOPMENTAL DISABILITIES ASSOCIATED WITH NEONATAL HYPOXIC-ISCHEMIC ENCEPHALOPATHY

(71) Applicant: Dompe' farmaceutici S.P.A., Milan (IT)

(72) Inventors: Andrea Aramini, LAquila (IT); Laura Brandolini, LAquila (IT); Serena Boccella, Naples (IT); Rubina Novelli, LAquila (IT)

(73) Assignee: Dompe' Farmaceutici S.P.A., Milan (IT)

( * ) Notice: Subject to any disclaimer, the term of this patent is extended or adjusted under 35 U.S.C. 154(b) by 0 days.

(21) Appl. No.: 19/091,464

(22) Filed: Mar. 26, 2025

(65) Prior Publication Data

US 2025/0304638 A1      Oct. 2, 2025

(30) Foreign Application Priority Data

Mar. 27, 2024      (EP) ..................................... 24167048

(51) Int. Cl.
| | |
|---|---|
| *C07K 14/48* | (2006.01) |
| *A61K 9/00* | (2006.01) |
| *A61K 38/00* | (2006.01) |
| *A61P 25/14* | (2006.01) |

(52) U.S. Cl.
CPC ............ *C07K 14/48* (2013.01); *A61K 9/0043* (2013.01); *A61P 25/14* (2018.01); *A61K 38/00* (2013.01)

(58) Field of Classification Search
CPC ...... C07K 14/48; A61K 9/0043; A61K 38/00; A61K 47/02; A61K 38/185; A61P 25/14
See application file for complete search history.

(56) References Cited

U.S. PATENT DOCUMENTS

2019/0022101 A1      1/2019   Kujawa et al.

FOREIGN PATENT DOCUMENTS

| | | |
|---|---|---|
| CA | 3053267 A1 | 8/2018 |
| CN | 1112215 C | 6/2003 |
| CN | 114933657 A | 8/2022 |
| EP | 3431494 A1 | 1/2019 |
| WO | WO 2000022119 A1 | 4/2000 |
| WO | WO 2013011536 A1 | 1/2013 |
| WO | WO 2013092776 A1 | 6/2013 |
| WO | WO 2018087656 A1 | 5/2018 |
| WO | WO 2018140792 A2 | 8/2018 |
| WO | WO 2018215414 A1 | 11/2018 |
| WO | WO 2019207106 A1 | 10/2019 |
| WO | WO 2021052926 A1 | 3/2021 |
| WO | WO 2022105847 A1 | 5/2022 |
| WO | WO 2024028487 A1 | 2/2024 |
| WO | WO 2024/062135 A1 | 3/2024 |

OTHER PUBLICATIONS

Holtzman et al., Ann. Neurol., 1996, 39:114-22.*
Manni et al., Front. Pharmacol., 2021, 12: 754502.*
Curatola et al., Biol. Direct, 2023, 18:24.*
Chiaretti et al. Brain injury, 2017, 31(11): 1538-47.*
Chiaretti et al., Archives Ital. de Biol, 2011, 149:275-82.*
Cheng et al., Neurol. Research, 2009, 31:753-8.*
Aldrin-Kirk et al., "Chemogenetic modulation of cholinergic interneurons reveals their regulating role on the direct and indirect output pathways from the striatum," Neurobiology of Disease, Jan. 2018, 109(A):148-162.
Allen et al., "Hypoxic Ischemic Encephalopathy: Pathophysiology and Experimental Treatments," Newborn Infant Nurs. Rev., Sep. 2011, 11(3):125-133.
Apfel et al., "Efficacy and Safety of Recombinant HumanNerve Growth Factor in Patients with Diabetic Polyneuropathy," JAMA, Nov. 2000, 284(17):2215-2221.
Azzopardi et al., "Moderate hypothermia to treat perinatal asphyxia encephalopathy," N. Engl. J. Med., Oct. 2009, 361(14):1349-58.
Bailey et al., "Behavioral Phenotyping of Transgenic and Knockout Mice: Practical Concerns and Potential Pitfalls," ILAR Journal, 2006, 47(2):124-131.
Blair et al., "Intrapartum asphyxia: a rare cause of cerebral palsy," J. Pediatr., Apr. 1988, 112(4):515-9.
Bruschettini et al., "Stem cell-based interventions for the prevention of morbidity and mortality following hypoxic-ischaemic encephalopathy in newborn infants (Review)," Cochrane Database of Systematic Reviews, Aug. 2020, 2020(8):CD013202.
Capsoni et al., "Intranasal "painless" Human Nerve Growth Factors Slows Amyloid Neurodegeneration and Prevents Memory Deficits in App X PS1 Mice," PLOS One, May 2012, 7(5):e37555, 16 pages.
Carloni et al., "Simvastatin reduces caspase-3 activation and inflammatory markers induced by hypoxia-ischemia in the newborn rat," Neurobiol. Dis., Jan. 2006, 21(1):119-26.
Chang et al., "A Review of Spasticity Treatments: Pharmacological and Interventional Approaches," Crit. Rev. Phys. Rehabil. Med., 2013, 25(1-2):11-22.
Chaplan et al., "Quantitative assessment of tactile allodynia in the rat paw," J. Neurosci. Methods, Jul. 1994, 53(1):55-63.
Crawley, et al., "What's wrong with my mouse? Behavioral phenotyping of transgenic and knockout mice," Genes, Brain and Behavior, 2002, 1:131-134.
Dutta et al., "Men and mice: Relating their ages," Life Science, May 2016, 152:244-8.
Extended European Search Report in European Appln. No. 22188990.0, mailed on Jan. 20, 2023, 15 pages.
Extended European Search Report in European Appln. No. 22197562.6, mailed on Mar. 7, 2023, 15 pages.

(Continued)

*Primary Examiner* — Olga N Chernyshev
(74) *Attorney, Agent, or Firm* — Fish & Richardson P.C.

(57) ABSTRACT

The present disclosure relates to nerve growth factor (NGF) for use in the prevention or treatment of neurodevelopmental disabilities associated with neonatal hypoxic-ischemic encephalopathy in a subject, wherein the NGF is administered intranasally to the subject.

23 Claims, 16 Drawing Sheets

Specification includes a Sequence Listing.

(56) References Cited

OTHER PUBLICATIONS

Finer et al., "Factors affecting outcome in hypoxic-ischemic encephalopathy in term infants," Am. J. Dis. Child., Jan. 1983, 137(1):21-5.

Gluckman et al., "Selective head cooling with mild systemic hypothermia after neonatal encephalopathy: multicentre randomised trial," Lancet., Feb. 2005, 365(9460):663-70.

Hahn, "Clinical Manifestations of Hypoxic-Ischemic Encephalopathy," Diagnosis of the Infant with Brain Injury, Dec. 2017, 16(3):247-257.

International Search Report and Written Opinion in International Appln. No. PCT/EP2023/071698, mailed on Oct. 12, 2023, 14 pages.

International Search Report and Written Opinion in International Appln. No. PCT/EP2023/076387, mailed on Nov. 23, 2023, 16 pages.

Jacobs et al., "Whole-body hypothermia for term and near-term newborns with hypoxic-ischemic encephalopathy: a randomized controlled trial," Arch. Pediatr. Adolesc. Med., Aug. 2011, 165(8):692-700.

Khalin et al., "A mouse model of weight-drop closed head injury emphasis on cognitive and neurological deficiency," Neural Regeneration Research, Apr. 2016, 11(4):630-635.

Khundadze et al., "Mouse models for hereditary spastic paraplegia uncover a role of PI4K2A in autophagic lysosome reformation," Autophagy, Mar. 2021, 17(11):3690-3706.

Lawn et al., "4 million neonatal deaths: when? Where? Why?" Neonatal Survival, Mar. 2005, 365(9462):891-900.

Li, "Spasticity, Motor Recovery, and Neural Plasticity after Stroke," Frontiers in Neurology, Apr. 2017, 8(120):1-8.

Llovera et al., "Results of a preclinical randomized controlled multicenter trial (pRCT): Anti-CD49d treatment for acute brain ischemia," Sci. Transl. Med., Aug. 2015, 7(299):299ra121.

Luigi et al., "Intranasal Delivery of Nerve Growth Factor in Neurodegenerative Diseases and Neurotrauma," Frontiers in Pharmacology, Nov. 2021, 12(754502):1-11.

Mathewson et al., "Pathophysiology of Muscle Contractures in Cerebral Palsy," Phys. Med. Rehabil. Clin. N. Am., Feb. 2015, 26(1):57-67.

Patak et al., "From Bedside to Bench: How Clinical Reality Should Instruct Stroke Modeling," Ulrich Dirnagl (ed.), Rodent Models of Stroke, Neuromethods, 2010, 286 pages.

PennMedicine.org [online], "Spasticity," Jan. 2023, retrieved on Apr. 15, 2025, retrieved from URL <https://www.pennmedicine.org/for-patients-and-visitors/patient-information/conditions-treated-a-to-z/spasticity>, 4 pages.

Ranjan et al., "Advances in Therapies to Treat Neonatal Hypoxic-Ischemic Encephalopathy," J. Clin. Med., Oct. 2023, 12(20):6653.

Rice et al., "The influence of immaturity on hypoxic-ischemic brain damage in the rat," Ann. Neurol., Feb. 1981, 9(2):131-41.

Roland et al., "Clinical aspects of perinatal hypoxic-ischemic brain injury," Seminars in Pediatric Neurology, Mar. 1995, 2(1):57-71.

Royl et al., "Effects of the PDE5-inhibitor vardenafil in a mouse stroke model," Brain Res., Apr. 2009, 1265:148-57.

Salvinelli et al., "Endogenous nerve growth factor stimulation: effects on auditory pathway neural cells in a mouse model," European Review for Medical and Pharmacological Sciences, Oct. 2018, 22(20):7013-7019.

Sarnat et al., "Neonatal encephalopathy following fetal distress. A clinical and electroencephalographic study," Arch. Neurol., Oct. 1976, 33(10):696-705.

Schaar et al., "Functional assessments in the rodent stroke model," Exp. Transl. Stroke Med., Jul. 2010, 2(1):13.

Shankaran et al., "Whole-body hypothermia for neonates with hypoxic-ischemic encephalopathy," N. Engl. J. Med., Oct. 2005, 353(15):1574-84.

Simbruner et al., "Systemic hypothermia after neonatal encephalopathy: outcomes of neo.nEURO.network RCT," Pediatrics., Oct. 2010, 126(4):e771-8.

Tang et al., "[Neonatal hypoxic ischemic encephalopathy treated with acupuncture combined with acupoint injection: a randomized controlled trial]," Randomized Controlled Trial-Zhongguo Zhen Jiu, Jul. 2015, 35(7):641-5 (Abstract).

Valente et al., "Harmonization of sensorimotor deficit assessment in a registered multicentre pre-clinical randomized controlled trial using two models of ischemic stroke," J Cereb. Blood Flow Metab., Jul. 2023, 43(7):1077-1088.

Vannucci et al., "Hypoxia-ischemia in the immature brain," J. Exp. Biol., Oct. 2004, 24(10):1090-7.

Vannucci et al., "Secondary energy failure after cerebral hypoxia-ischemia in the immature rat," J. Cereb. Blood Flow Metab., Oct. 2004, 24(10):1090-7.

Wieters et al., "Introduction to spasticity and related mouse models," Experimental Neurology, Jan. 2021, 335(112491):1-25.

Xu et al., "Neuroprotective Effects of a PSD-95 Inhibitor in Neonatal Hypoxic-Ischemic Brain Injury," Molecular Neurobiology, Nov. 2016, 53(9):5962-5970.

Anzilotti et al., "Genetic ablation of homeodomain-interacting protein kinase 2 selectively induces apoptosis of cerebellar Purkinje cells during adulthood and generates an ataxic-like phenotype," Cell Death and Disease, Dec. 2015, 6(12):e2004, 11 pages.

Chiaretti et al., "Intranasal nerve growth factor administration improves neurological outcome after GBS meningitis," Child's Nervous System, Apr. 2020, 36:2083-2088.

Davidson et al., "Update on mechanisms of the pathophysiology of neonatal encephalopathy," Seminars in Fetal and Neonatal Medicine, Oct. 2021, 26(5):101267, 7 pages.

Gatto et al., "Intranasal human-recombinant NGF administration improves outcome in children with post-traumatic unresponsive wakefulness syndrome," Biology Direct, Oct. 2023, 18(1):61, 14 pages.

Giampa et al., "Inhibition of the Striatal Specific Phosphodiesterase PDE10A Ameliorates Striatal and Cortical Pathology in R6/2 Mouse Model of Huntington's Diseasee," PLoS One, Oct. 2010, 5(10):e13417, 14 pages.

Manni et al., "Acute intranasal treatment with nerve growth factor limits the onset of traumatic brain injury in young rats," British Pharmacological Society, Feb. 2023, 180:1949-1964.

Manni et al., "Intranasal nerve growth factor for prevention and recovery of the outcomes of traumatic brain injury," Neural Regeneration Research, Apr. 2023, 18(4):773-778.

Qiuying et al., "Clinical effect of head hypothermia combined with mouse nerve growth factor in the treatment of neonatal moderately severe hypoxic ischemic encephalopathy," Chinese Journal of Primary Medicine and Pharmacy, Feb. 2017, 24(3), 10 pages.

Tetorou et al., "Current Therapies for Neonatal Hypoxic-Ischaemic and Infection-Sensitised Hypoxic-Ischaemic Brain Damage," Frontiers in Synaptic Neuroscience, Aug. 2021, 13(709301):1-30.

Wang et al., "Intervention of NGF and Don-Shen Root in Hypoxic-Ischemic Encephalopathy of Newborn Rat," Chinese Journal of Contemporary Pediatrics, 2000, 2(4): 263-266 (English abstract translation).

Yin et al., "Effect of mouse nerve growth factor on the expression of glial fibrillary acidic protein in hippocampus of neonatal rats with hypoxic-ischemic brain damage," Experimental and Therapeutic Medicine, Feb. 2013, 5(2):419-422.

Yin et al., "Role of mouse nerve growth factor in neural recovery following hypoxic-ischemic brain damage," International Journal of Clinical and Experimental Medicine, Oct. 2013, 6(10):951-955.

Huang et al., "Neurotrophins: Roles in Neuronal Development and Function," Annu. Rev. Neurosci., 2001, 24:677-736.

International Search Report and Written Opinion in International Appln. No. PCT/IB2025/053216, mailed on Jun. 16, 2025, 14 pages.

* cited by examiner

FIG. 15A health score_mean score

FIG. 15B health score_mean score

FIG. 15C Forest plot

SEQUENCE LISTING

```
Sequence total quantity: 2
SEQ ID NO: 1              moltype = AA  length = 118
FEATURE                  Location/Qualifiers
source                   1..118
                         mol_type = protein
                         organism = synthetic construct
SEQUENCE: 1
SSSHPIFHRG EFSVCDSVSV WVGDKTTATD IKGKEVMVLG EVNINNSVFK QYFFETKCRD  60
PNPVDSGCRG IDSKHWNSYC TTTHTFVKAL TMDGKQAAWR FIRIDTACVC VLSRKAVR    118

SEQ ID NO: 2              moltype = AA  length = 120
FEATURE                  Location/Qualifiers
source                   1..120
                         mol_type = protein
                         organism = synthetic construct
SEQUENCE: 2
SSSHPIFHRG EFSVCDSVSV WVGDKTTATD IKGKEVMVLG EVNINNSVFK QYFFETKCRD  60
PNPVDSGCRG IDSKHWNSYC TTTHTFVKAL TMDGKQAAWR FIRIDTACVC VLSRKAVRRA  120
```

NERVE GROWTH FACTOR AND METHODS OF USE THEREOF FOR NEURODEVELOPMENTAL DISABILITIES ASSOCIATED WITH NEONATAL HYPOXIC-ISCHEMIC ENCEPHALOPATHY

CROSS-REFERENCE TO RELATED APPLICATION

This application claims priority to European Patent Application No. 24167048.8, filed Mar. 27, 2024. The contents of this application are incorporated herein by reference in their entireties.

SEQUENCE LISTING

This application contains a Sequence Listing that has been submitted electronically as an XML file named "36381-0060001. XML." The XML file, created on Mar. 25, 2025, is 3,052 bytes in size. The material in the XML file is hereby incorporated by reference in its entirety.

FIELD OF THE INVENTION

The present disclosure relates to the prevention and/or treatment of neurodevelopmental disabilities associated with neonatal hypoxic-ischemic encephalopathy in a subject.

The present disclosure relates to the prevention and/or treatment of motor impairment associated with neonatal hypoxic-ischemic encephalopathy in a subject.

The present disclosure further relates to the prevention and/or treatment of cerebral palsy (CP) associated with neonatal hypoxic-ischemic encephalopathy in a subject.

The present disclosure further relates to promoting neurodevelopment in a subject affected by neonatal hypoxic-ischemic encephalopathy.

BACKGROUND

Neonatal hypoxic-ischemic encephalopathy (HIE) is a devastating condition affecting newborns.

HIE is caused by inadequate blood supply (ischemia) and oxygen supply (hypoxia) to the brain of the fetus or infant during or after birth, which determine the establishment of a brain injury (Finer, N N et al., Am J Dis Child 1983; 137:21-5; Lawn, J. E. et al., Lancet 2005, 365, 891-900; Ranjan, K. et al., J. Clin. Med. 2023, 12, 6653; Jin S. Hahn Clinical Manifestations of Hypoxic-Ischemic Encephalopathy, Fetal and Neonatal Brain Injury, pp. 247-257, from Section 3—Diagnosis of the Infant with Brain Injury, Published online by Cambridge University Press: 13 Dec. 2017).

The severity of HIE depends on various factors, such as the aetiology, extent of hypoxia/ischemia, maturation phase of the brain, regional cerebral blood flow, and maternal diseases/factors affecting the fetus (Allen, K. A. et al., Newborn Infant Nurs. Rev. 2011, 11, 125-133).

HIE affects both premature and full-term neonates, and the occurrence of this condition is found in both developed and developing countries, with a higher incidence in the latter. Several factors are known to intervene in the onset of HIE, such as placental abruption, prolapse of the umbilical cord and uterine rupture (Ranjan, K. et al., J. Clin. Med. 2023, 12, 6653).

A large percentage of infants with HIE die within the first two years of life, and most of those who live longer develop a range of neurodevelopmental disabilities, such as motor impairment, mental retardation, epilepsy, cerebral palsy, and learning disabilities (Bruschettini, M. et al., Cochrane Database Syst. Rev. 2020, 8, Cd013202; Allen, K. A. et al., Newborn Infant Nurs. Rev. 2011, 11, 125-133).

Based on clinical manifestation, HIE is classified into three levels according to the scoring system developed by Sarnat and Sarnat (Sarnat H B, Sarnat M S. Arch Neurol 1976; 33:696-705), namely mild (stage 1), moderate (stage 2) or severe (stage 3) HIE. The classification is mainly based on the following clinical features: the infant's level of consciousness, cranial nerve findings, muscle tone, deep tendon reflexes, neonatal reflexes, spontaneous motor activity, and autonomic function (see Table 16.1 of Jin S. Hahn Clinical Manifestations of Hypoxic-Ischemic Encephalopathy, Fetal and Neonatal Brain Injury, pp. 247-257, from Section 3-Diagnosis of the Infant with Brain Injury, Published online by Cambridge University Press: 13 Dec. 2017).

One of the most debilitating clinical manifestations experienced by patients with HIE is motor impairment, which is typically caused by muscle tone deregulation. This symptom is not identical in every patient, but varies according to the severity of HIE. In fact, muscle tone is one of the parameters considered to stratify patients into the three stages of HIE defined by Sarnat and Sarnat. Specifically, muscle tone is typically normal or hypertonic in patients with mild HIE, hypotonic in patients with moderate HIE, and flaccid in patients with severe HIE (Sarnat H B, Sarnat M S. Arch Neurol 1976; 33:696-705; Roland E H, Hill A. Semin Pediatr Neurol 1995; 2:57-71; Shankaran S, et al. N Engl J Med 2005; 353:1574-84; Allen, K. A. et al., Newborn Infant Nurs. Rev. 2011, 11, 125-133).

In addition, motor impairment can be more or less severe depending on the type of brain damage elicited by the hypoxic-ischemic event. Patients with periventricular leukomalacia (PVL) can develop spastic cerebral palsy (CP) in the form of diplegia, quadriplegia, or hemiplegia. Basal ganglia (BG) and thalamic involvement result in extrapyramidal symptoms. Multicystic encephalopathy is associated with quadriplegia (Blair E, Stanley F J. J Pediatr 1988; 112:515-19).

Despite the fact that to date the use of therapeutic hypothermia has been approved and other therapeutic options for the treatment of HIE are under investigation (Ranjan et al., J. Clin. Med. 2023, 12, 6653), the rates of neonates who experience neurodevelopmental disability associated with neonatal hypoxic-ischemic encephalopathy such as cognitive disfunction, cerebral palsy and moderate/severe disability is still unacceptably high (Gluckman P D et al., Lancet. 2005; 365(9460):663-670; Jacobs S E et al., Arch Pediatr Adolesc Med. 2011, 165(8):692-700; Simbruner G. et al., Pediatrics, 2010; 126(4):e771-778; Azzopardi D V et al., N Engl J Med. 2009; 361(14):1349-1358). Furthermore, the management of motor impairment associated with this condition is still not satisfactory since it is complicated by its heterogeneity in different patients.

It is therefore felt the need of developing new effective, long lasting and safe therapeutic approaches for the prevention or treatment of neurodevelopmental disabilities associated with (e.g., caused by) HIE., such as motor impairment or cerebral palsy.

SUMMARY

As it will be described in the experimental section, the present inventors have found that when NGF is administered intranasally to subjects who experienced NHIE at birth, it is effective in reducing the incidence of major neurodevelopmental disabilities, such as cerebral palsy, motor impairment and intellectual disability. In particular, the present inventors have also found that when NGF is administered intranasally, it is delivered at particularly high concentrations to the areas of the brain that are compromised in patients with motor impairment associated with (e.g., affected or caused by) neonatal hypoxic-ischemic encephalopathy (HIE).

The present inventors have also surprisingly found that the intranasal administration of NGF is effective in the prevention or treatment of motor impairment associated with (e.g., affected or caused by) HIE, regardless of the specific clinical manifestation of the motor impairment that the patient experiences. This is due to the efficacy of the intranasal administration of NGF in normalizing the muscle tone of patients affected by HIE, thereby improving their motor ability. Based on the obtained data, the intranasal administration of NGF is therefore able to prevent and/or treat motor impairment associated with (e.g., affected or caused by) HIE in patients affected by this condition.

Accordingly, object of the disclosure is NGF for use in the prevention and/or treatment of a neurodevelopmental disability associated with (e.g., affected or caused by) neonatal hypoxic-ischemic encephalopathy in a subject.

A further object of the disclosure is NGF for use in the prevention and/or treatment of a motor impairment associated with (e.g., affected or caused by) HIE.

A further object of the disclosure is NGF for use in the prevention and/or treatment of cerebral palsy (CP) associated with (e.g., affected or caused by) neonatal hypoxic-ischemic encephalopathy in a subject.

A further object of the disclosure is NGF for use in promoting neurodevelopment in a subject diagnosed with neonatal hypoxic-ischemic encephalopathy Disclosed herein is a method is described for preventing or treating neurodevelopmental disabilities associated with neonatal hypoxic-ischemic encephalopathy (NHIE) in a subject in need, involving the intranasal administration of a therapeutically or prophylactically effective amount of nerve growth factor (NGF). These neurodevelopmental disabilities can include motor impairment or delayed neurodevelopment, including conditions such as cerebral palsy. Additionally, the disabilities can encompass cognitive, behavioral, or sensory impairments. Motor impairment is associated with muscle tone deregulation, and the administration of NGF aims to reduce the likelihood or severity of these neurodevelopmental disabilities compared to subjects who do not receive NGF, particularly those diagnosed with NHIE.

Subjects at risk of developing such disabilities can also benefit from NGF administration, especially those who have experienced perinatal depression, as indicated by factors such as an Apgar score below 5 at 10 minutes of age, need for resuscitation (including chest compressions, mechanical ventilation, or CPAP), a pH below 7.00 in cord or neonatal blood gas within 60 minutes of birth, or a base deficit exceeding 15 mmol/L. The need for resuscitation can include chest compressions, mechanical ventilation, or CPAP therapy. The method is particularly applicable to subjects diagnosed with NHIE classified as stage 2 or 3 according to the Modified Sarnat staging, with a gestational age at birth of at least 36 weeks and a birth weight of at least 1800 grams.

For subjects diagnosed with motor impairment or cerebral palsy associated with NHIE, NGF is administered intranasally for therapeutic purposes. It can also be used for preventing cerebral palsy in subjects identified as being at risk due to NHIE. The administration of NGF is particularly relevant for subjects who have received therapeutic hypothermia within the first six hours after birth. The initial administration of NGF occurs within one month of birth, preferably within seven days, more preferably within 72 hours, even more preferably within 36 hours, and most preferably within 24 hours of birth. Alternatively, NGF can be administered for the first time between one month and 36 months of age, with further preferences for administration within one to 24 months, one to 12 months, one to six months, or one to four months, with an additional preference for administration between three and nine months, ideally between three and six months of age.

The administration regimen can follow a continuous schedule with two or more cycles of one-week treatment periods or an intermittent schedule with treatment cycles interspersed with washout periods. A preferred intermittent regimen includes at least three cycles, each consisting of seven days of daily NGF administration followed by 21 days of washout. The total NGF dose administered ranges from 25 μg/kg to 400 μg/kg, with preferred ranges of 30 μg/kg to 300 μg/kg, 35 μg/kg to 200 μg/kg, 40 μg/kg to 100 μg/kg, 40 μg/kg to 60 μg/kg, and 45 μg/kg to 55 μg/kg, with a most preferred dose of 50 μg/kg. The dose per cycle is between 15 μg/kg and 20 μg/kg, preferably 16 μg/kg to 17 μg/kg, even more preferably 16.6 μg/kg to 16.8 μg/kg, with a most preferred dose of 16.7 μg/kg. The daily dose is between 2 μg/kg and 3 μg/kg, preferably 2.3 μg/kg to 2.5 μg/kg, with a most preferred dose of 2.4 μg/kg. The dose per nostril is between 0.3 μg/kg/nostril and 1 μg/kg/nostril, preferably 0.4 μg/kg/nostril to 0.8 μg/kg/nostril, more preferably 0.5 μg/kg/nostril to 0.7 μg/kg/nostril, with a most preferred dose of 0.6 μg/kg/nostril. The daily NGF dose is administered twice daily with a 12-hour interval.

The treatment aims to normalize muscle tone in subjects with NHIE and address motor impairment or muscle tone deregulation associated with cerebral palsy. Muscle tone deregulation can include conditions such as hypotonia, flaccidity, hypertonia, dystonia, ataxia, extrapyramidal symptoms, diplegia, tetraplegia, quadriplegia, hemiplegia, and paraplegia. Hypotonia can be focal or general, dystonia can be focal, segmental, or general, and hypertonia can include spasticity, rigidity, or paratonia.

In some instances, NGF is formulated as a pharmaceutical composition for intranasal administration, comprising at least one pharmaceutically acceptable excipient. The NGF concentration in the composition ranges from 5 μg/ml to 1 mg/ml, preferably from 10 μg/ml to 400 μg/ml, even more preferably from 15 μg/ml to 200 μg/ml. The composition can consist of NGF, sodium chloride, phosphate buffer, and water. The NGF used is human NGF, preferably recombinant human NGF, and comprises or consists of the amino acid sequence of SEQ ID NO:1 or SEQ ID NO:2.

In some instances, also disclosed is a method for treating cerebral palsy associated with neonatal hypoxic-ischemic encephalopathy involves administering a therapeutically effective amount of nerve growth factor (NGF) intranasally to a subject in need. In some instances, the NGF used in this method includes the sequence identified as SEQ ID NO:1. This treatment can also reduce the likelihood or severity of cerebral palsy in such subjects compared to those who have not received NGF, particularly those diagnosed with neonatal hypoxic-ischemic encephalopathy.

The method applies to subjects experiencing motor impairments caused by muscle tone deregulation, which can include conditions such as hypotonia, flaccidity, hypertonia, dystonia, ataxia, extrapyramidal symptoms, diplegia, tetraplegia, quadriplegia, hemiplegia, and paraplegia. Hypotonia can be focal or general, dystonia can be focal, segmental, or general, and hypertonia can manifest as spasticity, rigidity, or paratonia. The administration of NGF aims to normalize muscle tone in affected subjects to levels comparable to those of healthy subjects of the same age.

The treatment is applicable to subjects who have experienced perinatal depression, as indicated by criteria such as an Apgar score below 5 at 10 minutes of age, a need for resuscitation at 10 minutes, a cord blood pH below 7.00, or a base deficit meeting specific thresholds. Eligible subjects generally have a gestational age of at least 36 weeks and a birth weight of at least 1800 grams.

NGF administration can begin within the first 24 hours after birth or between one and four months of age. The administration schedule can be continuous, involving two or more one-week treatment cycles, or intermittent, involving treatment cycles alternated by wash-out periods. The total NGF dose ranges from 25 µg/kg to 400 µg/kg, with per-cycle doses between 15 µg/kg and 20 µg/kg and daily doses between 2 µg/kg and 3 µg/kg. Additionally, subjects undergoing this treatment can also receive therapeutic hypothermia within the first six hours after birth.

The NGF can be formulated as a pharmaceutical composition containing at least one pharmaceutically acceptable excipient, which can include sodium chloride, phosphate buffer, and water.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

DETAILED DESCRIPTION

Figure 1:
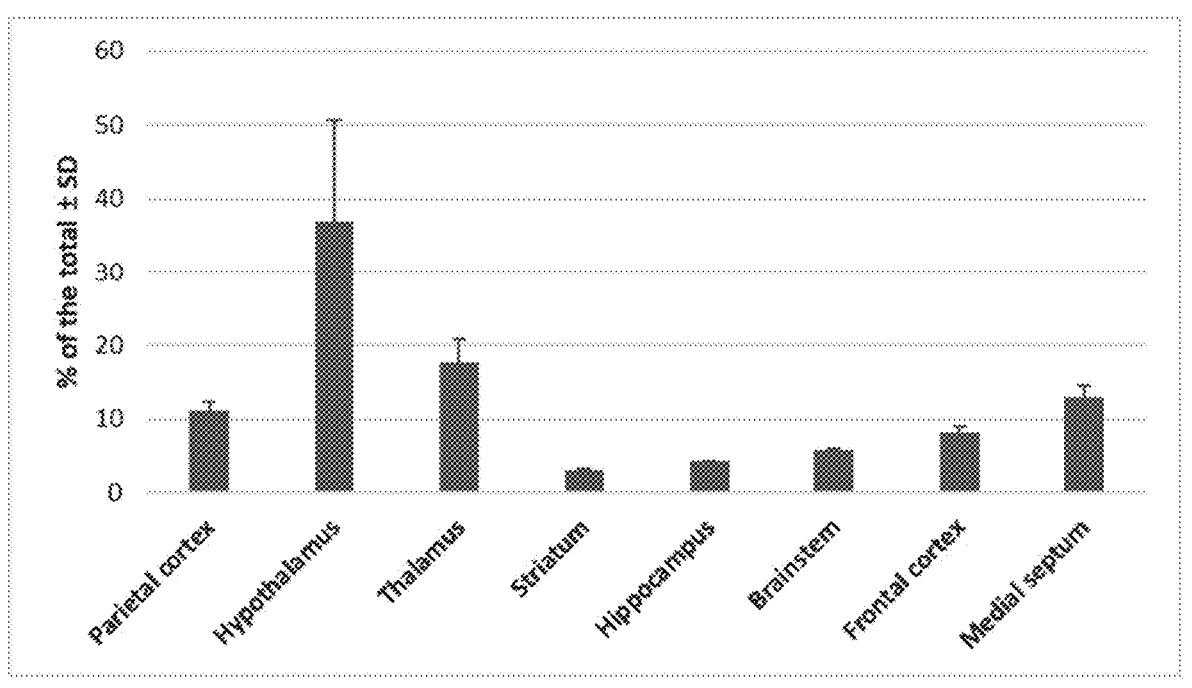
FIG. 1 shows NGF biodistribution in rat brain areas after intranasal administration, measured by ELISA over 24 hours, as described in Example 1. Results are expressed as percent of the total amount absorbed over 24 hours in the rat brain after administration.

The present inventors have found that the intranasal administration of nerve growth factor (NGF) is effective in n preventing, ameliorating, or treating neurodevelopmental disability associated with (e.g. affected or caused by) neonatal hypoxic-ischemic encephalopathy (HIE) and clinical manifestations thereof, such as motor impairment and cerebral palsy. Also, as will be explained below, the inventors have surprisingly found that a schedule of administration wherein NGF is first administered intranasally at least one month after the occurrence of the damage (late administration) exerts beneficial effects in this pathological setting.

The terms "treatment" and "prevention" as used herein refer to the eradication/amelioration or prevention/delay in onset, respectively, of a disorder or of one or more of the symptoms associated thereof.

Treatment includes therapeutic measures that cure, slow down, lessen the severity of, and/or halt progression of a diagnosed pathologic condition or disorder. Prevention includes prophylactic or preventative measures that prevent, reduce the likelihood of occurrence, reduce the severity of occurrence, and/or slow the development of a targeted pathologic condition or disorder.

In the context of the present application, the following definitions apply.

As used herein, "slowing down" refers to the slowing down the progress of neurodevelopmental disability (e.g., mild delays in motor development, damage, dysfunction, or developmental abnormalities within the nervous system, difficulties in movement, muscle coordination, and motor skills, which can include spasticity, weakness, poor muscle tone), preferably motor impairment, cerebral palsy and cognitive impairment, associated with (e.g. affected or caused by) neonatal hypoxic-ischemic encephalopathy (HIE) in a subject, e.g., a human subject, diagnosed with neonatal hypoxic ischemic encephalopathy receiving NGF for use as described herein as compared to a population diagnosed with neonatal hypoxic-ischemic encephalopathy (HIE) of comparable severity not receiving NGF for use as described herein.

As used herein, "lessening the severity" refers to the lessening of the severity of neurodevelopmental disability (e.g., mild delays in motor development, damage, dysfunction, or developmental abnormalities within the nervous system, difficulties in movement, muscle coordination, and motor skills, which can include spasticity, weakness, poor muscle tone), preferably motor impairment, cerebral palsy and cognitive impairment, associated with (e.g. affected or caused by) neonatal hypoxic-ischemic encephalopathy (HIE) in a subject, e.g., a human subject, diagnosed with neonatal hypoxic ischemic encephalopathy receiving NGF for use as described herein as compared to a population diagnosed with neonatal hypoxic-ischemic encephalopathy (HIE) of comparable severity not receiving NGF for use as described herein.

As used herein "halting" refers to stopping progress of neurodevelopmental disability (e.g., mild delays in motor development, damage, dysfunction, or developmental abnormalities within the nervous system, difficulties in movement, muscle coordination, and motor skills, which can include spasticity, weakness, poor muscle tone), preferably motor impairment, cerebral palsy and cognitive impairment, associated with (e.g. affected or caused by) neonatal hypoxic-ischemic encephalopathy (HIE) in a subject, e.g., a human subject, diagnosed with neonatal hypoxic ischemic encephalopathy receiving NGF for use as described herein as compared to a population diagnosed with neonatal hypoxic-ischemic encephalopathy (HIE) of comparable severity not receiving NGF for use as described herein.

As used herein "slowing the development" refers to slowing the development of neurodevelopmental disability (e.g., mild delays in motor development, damage, dysfunction, or developmental abnormalities within the nervous system, difficulties in movement, muscle coordination, and motor skills, which can include spasticity, weakness, poor muscle tone), preferably motor impairment, cerebral palsy and cognitive impairment, associated with (e.g. affected or caused by) neonatal hypoxic-ischemic encephalopathy (HIE) in a subject, e.g., a human subject, diagnosed with neonatal hypoxic ischemic encephalopathy receiving NGF for use as described herein as compared to a population diagnosed with neonatal hypoxic-ischemic encephalopathy (HIE) of comparable severity not receiving NGF for use as described herein.

As used herein, "reduce the likelihood of occurrence" refers to a reduction of the likelihood that a subject, e.g., a human subject, diagnosed with neonatal hypoxic ischemic encephalopathy receiving NGF for use as described herein will develop neurodevelopmental disability (e.g., mild delays in motor development, damage, dysfunction, or developmental abnormalities within the nervous system, difficulties in movement, muscle coordination, and motor skills, which can include spasticity, weakness, poor muscle tone), preferably motor impairment, cerebral palsy and cognitive impairment, associated with (e.g. affected or caused by) neonatal hypoxic-ischemic encephalopathy (HIE), compared to a population diagnosed with neonatal hypoxic-ischemic encephalopathy (HIE) not receiving NGF for use as described herein.

Preferably, said NGF reduces by at least 40%, preferably by at least 50%, more preferably by at least 60%, even more preferably by at least 70%, even more preferably by at least 80% the likelihood for the subject to have neurodevelopmental disability, preferably motor impairment, cerebral palsy and cognitive impairment, associated with (e.g. affected or caused by) neonatal hypoxic-ischemic encephalopathy (HIE).

As used herein, "reduce the severity of occurrence" refers to the case where a subject diagnosed with neonatal hypoxic ischemic encephalopathy receiving NGF for use as described herein develops a neurodevelopmental disability (e.g., mild delays in motor development, damage, dysfunction, or developmental abnormalities within the nervous system, difficulties in movement, muscle coordination, and motor skills, which can include spasticity, weakness, poor muscle tone), preferably motor impairment, cerebral palsy and cognitive impairment, associated with (e.g. affected or caused by) neonatal hypoxic-ischemic encephalopathy after NGF treatment, substantially reduced in severity as compared to a population diagnosed with neonatal hypoxic-ischemic encephalopathy (HIE) of comparable severity not receiving NGF for use as described herein.

A therapeutically effective amount refers to an amount of NGF effective to treat a disease or disorder in a subject (e.g., a mammal; e.g., a human).

A prophylactically effective amount refers to an amount effective, at dosages and for periods of time necessary, to achieve the desired prophylactic result.

A first object of the present disclosure relates to nerve growth factor (NGF) for use in the prevention and/or treatment of neurodevelopmental disability associated with (e.g. affected or caused by) neonatal hypoxic-ischemic encephalopathy (HIE) in a subject, wherein said NGF is administered intranasally to the subject.

In some instances, the present disclosure relates to NGF for use in curing neurodevelopmental disability associated with (e.g. affected or caused by) neonatal hypoxic-ischemic encephalopathy (HIE) in a subject, wherein said NGF is administered intranasally to the subject.

In some instances, the present disclosure relates to NGF for use in slowing down neurodevelopmental disability associated with (e.g. affected or caused by) neonatal hypoxic-ischemic encephalopathy (HIE) in a subject, wherein said NGF is administered intranasally to the subject.

In some instances, the present disclosure relates to NGF for use in lessening the severity of neurodevelopmental disability associated with (e.g. affected or caused by) neonatal hypoxic-ischemic encephalopathy (HIE) in a subject, wherein said NGF is administered intranasally to the subject.

In some instances, the present disclosure relates to NGF for use in halting progression of neurodevelopmental disability associated with (e.g. affected or caused by) neonatal hypoxic-ischemic encephalopathy (HIE) in a subject, wherein said NGF is administered intranasally to the subject.

In some instances, the present disclosure relates to NGF for use in slowing the development of neurodevelopmental disability associated with (e.g. affected or caused by) neonatal hypoxic-ischemic encephalopathy (HIE) in a subject, wherein said NGF is administered intranasally to the subject.

In some instances, the present disclosure relates to NGF for use in reducing the likelihood of occurrence of neurodevelopmental disability associated with (e.g. affected or caused by) neonatal hypoxic-ischemic encephalopathy (HIE) in a subject, wherein said NGF is administered intranasally to the subject.

In some instances, the present disclosure relates to NGF for use in reducing the severity of occurrence of neurodevelopmental disability associated with (e.g. affected or caused by) neonatal hypoxic-ischemic encephalopathy (HIE) in a subject, wherein said NGF is administered intranasally to the subject.

In some instances, the subject is a human subject, preferably a neonate or an infant.

In some instances, said neurodevelopmental disability is selected from the group consisting of cerebral palsy, cognitive impairment, motor impairment, delayed neurodevelopment, behavioral impairment and sensory impairment.

In some instances, said motor impairment is as described below.

In some instances, said cerebral palsy is as described below.

In some instances, said subject has been diagnosed with neurodevelopmental disability associated with (e.g. affected or caused by) neonatal hypoxic-ischemic encephalopathy (HIE) and said NGF is for use in the treatment of said neurodevelopmental disability in said subject, by intranasal administration to said subject.

Said treatment can include one or more of the following: curing, slowing down, lessening the severity of, halting the progression of neurodevelopmental disability in said subject.

In some instances, said subject has been identified as being at risk of developing neurodevelopmental disability associated with (e.g. affected or caused by) neonatal hypoxic-ischemic encephalopathy (HIE) and said NGF is for use in the prevention of said neurodevelopmental disability in said subject, by intranasal administration to said subject.

Said prevention can include one or more of the following: reducing the likelihood of occurrence, reducing the severity of occurrence, slowing the development of neurodevelopmental disability in said subject.

In some instances, said subject has been identified as being at risk of developing neurodevelopmental disability associated with (e.g. affected or caused by) neonatal hypoxic-ischemic encephalopathy (HIE) and said NGF is for use in the reduction of the likelihood and/or reduction of severity of occurrence of said neurodevelopmental disability in said subject, by intranasal administration to said subject.

In some instances, the present disclosure provides a method for preventing and/or treating neurodevelopmental disability associated with (e.g. affected or caused by) neonatal hypoxic-ischemic encephalopathy in a subject through the intranasal administration of nerve growth factor (NGF). This method involves delivering NGF to the subject to promote neuronal survival, support neurogenesis, and enhance synaptic plasticity in regions of the brain affected by neurodevelopmental disability. NGF is administered by intranasal delivery, which allows for efficient transport across the blood-brain barrier and direct targeting of the central nervous system. The treatment aims to address a range of neurodevelopmental disabilities, including cognitive, motor, and sensory impairments, by stimulating the repair of damaged neural circuits and promoting the regeneration of lost or damaged neurons. The method can involve a series of intermittent NGF administration cycles, where the subject receives treatment over a period of time to maximize the neuroprotective and restorative effects while minimizing potential adverse reactions.

"Neurodevelopmental disability" refers to a broad category of conditions characterized by impaired brain function, which can affect cognitive, motor, sensory, or behavioral abilities. In some instances, said neurodevelopmental disability is selected from the group consisting of cerebral palsy, cognitive impairment, motor impairment, delayed neurodevelopment, behavioral impairment and sensory impairment.

These conditions result from damage, dysfunction, or developmental abnormalities within the nervous system, leading to long-term or permanent disability. Treatment of neurodevelopmental disability aims to restore or enhance neurological function, alleviate symptoms, and improve the overall quality of life for affected individuals.

A further object of the disclosure is nerve growth factor (NGF) for use in the prevention and/or treatment of motor impairment associated with (e.g., affected or caused by) neonatal hypoxic-ischemic encephalopathy (HIE) in a subject, wherein the NGF is administered intranasally to the subject.

"Motor impairment" in the setting of neonatal hypoxic-ischemic encephalopathy (HIE) refers to the loss or dysfunction of motor control resulting from brain injury caused by a lack of oxygen and blood flow to the brain during or shortly after birth. In the context of neonatal HIE, motor impairment manifests as difficulties in movement, muscle coordination, and motor skills, which can include spasticity, weakness, poor muscle tone (hypotonia or hypertonia), or motor delays. Motor impairment in neonatal HIE can vary in severity, from mild delays in motor development to more severe conditions, such as cerebral palsy, and can impact the ability of the infant to perform basic movements such as crawling, walking, or controlling voluntary muscle actions. The degree and type of motor impairment depend on the extent of the brain injury and the timing of the hypoxic-ischemic event during neurodevelopment.

In some instances, the present disclosure relates to NGF for use in curing motor impairment associated with (e.g. affected or caused by) neonatal hypoxic-ischemic encephalopathy (HIE) or one or more symptoms thereof in a subject, wherein the NGF is administered intranasally to the subject.

In some instances, the present disclosure relates to NGF for use in slowing down motor impairment associated with (e.g. affected or caused by) neonatal hypoxic-ischemic encephalopathy (HIE) or one or more symptoms thereof in a subject, wherein the NGF is administered intranasally to the subject.

In some instances, the present disclosure relates to NGF for use in lessening the severity of motor impairment associated with (e.g. affected or caused by) neonatal hypoxic-ischemic encephalopathy (HIE) or one or more symptoms thereof in a subject, wherein the NGF is administered intranasally to the subject.

In some instances, the present disclosure relates to NGF for use in halting the progression of motor impairment associated with (e.g. affected or caused by) neonatal hypoxic-ischemic encephalopathy (HIE) or of one or more symptoms associated thereof in a subject, wherein the NGF is administered intranasally to the subject.

In some instances, the present disclosure relates to NGF for use in slowing the development of motor impairment associated with (e.g. affected or caused by) neonatal hypoxic-ischemic encephalopathy (HIE) or one or more symptoms thereof in a subject, wherein the NGF is administered intranasally to the subject.

In some instances, the present disclosure relates to NGF for use in reducing the likelihood of occurrence of motor impairment associated with (e.g. affected or caused by) neonatal hypoxic-ischemic encephalopathy (HIE) or one or more symptoms thereof in a subject, wherein the NGF is administered intranasally to the subject.

In some instances, the present disclosure relates to NGF for use in reducing the severity of occurrence of motor impairment associated with (e.g. affected or caused by) neonatal hypoxic-ischemic encephalopathy (HIE) or one or more symptoms thereof in a subject, wherein the NGF is administered intranasally to the subject.

In some instances, said one or more symptoms thereof are selected from the group consisting of difficulties in movement, difficulties in muscle coordination, difficulties in motor skills, weakness, poor muscle tone and motor delays.

In some instances, the subject is a human subject. "Subject" as used herein refers to any animal (e.g., a mammal), including, but not limited to humans, non-human primates, and the like, which is to be the recipient of a particular treatment. Typically, the terms "subject" and "patient" are used interchangeably herein in reference to a human subject.

In some instances, the human subject is a neonate or an infant.

In some instances, the motor impairment is caused by a muscle tone deregulation.

In some instances, the NGF is for use in normalizing the muscle tone of a subject with neonatal hypoxic-ischemic encephalopathy (HIE). Normalizing includes returning the muscle tone of the subject to a level substantially comparable to the muscle tone of a healthy subject of the same age.

In some instances, the NGF is for use in improving motor impairment associated with (e.g. affected or caused by) neonatal hypoxic-ischemic encephalopathy (HIE) to a level compatible with the execution of daily activities typical of a subject of the same age who is not diagnosed with neonatal hypoxic-ischemic encephalopathy (HIE). In some instances, the daily activities include basic movements such as crawling, walking, or controlling voluntary muscle actions, sitting straight, eating, grasping objects and interacting with the surrounding environment.

In some instances, the motor impairment or the muscle tone deregulation is associated with (e.g., affected or caused by) cerebral palsy.

Cerebral palsy is a group of disorders that affect movement and muscle tone, often caused by brain damage or abnormal brain development. The intranasal administration of NGF offers a potential therapeutic intervention for subjects suffering from this debilitating condition.

In some instances, the muscle tone deregulation is selected from the group consisting of hypotonia, flaccidity, hypertonia, dystonia, ataxia, extrapyramidal symptoms, diplegia, tetraplegia, quadriplegia, hemiplegia and paraplegia.

In some instances, the hypotonia is selected from focal hypotonia and general hypotonia.

Focal hypotonia affects specific muscle groups, while general hypotonia affects the entire body. Both types of hypotonia can impair motor function and lead to difficulty with movement, balance, and coordination. NGF administration can help normalize muscle tone and improve overall motor performance in subjects affected by these conditions.

In some instances, the dystonia is selected from focal dystonia, segmental dystonia and general dystonia.

Focal dystonia affects a specific part of the body, segmental dystonia affects multiple regions of the body, and general dystonia involves widespread muscle involvement.

NGF has the potential to alleviate the symptoms of these types of dystonia and restore more functional muscle control.

In some instances, the hypertonia is selected from spasticity, rigidity and paratonia. Spasticity, rigidity, and paratonia can cause muscle stiffness and resistance to movement. NGF treatment can help reduce these symptoms by regulating the neural circuits involved in muscle tone, thus improving motor control and functionality.

In some instances, the subject has been diagnosed with a motor impairment associated with (e.g. affected or caused by) neonatal hypoxic ischemic encephalopathy (HIE) and the NGF is for use in the treatment of motor impairment in the subject, by intranasal administration to the subject.

Said treatment can include one or more of the following: curing, slowing down, lessening the severity of, halting the progression of motor impairment in the subject.

In some instances, according to this embodiment, the NGF is administered to the subject starting less than two years after birth, preferably less than one year after birth, more preferably less than eight months after birth, more preferably less than six months after birth, even more preferably between three and six months after birth.

In some instances, the subject has been identified as being at risk of developing a motor impairment associated with (e.g. affected or caused by) neonatal hypoxic ischemic encephalopathy (HIE) and the NGF is for use in the prevention of motor impairment in the subject prior to the development of the motor impairment, by intranasal administration to the subject.

Said prevention can include one or more of the following: reducing the likelihood of occurrence, reducing the severity of occurrence, slowing the development of motor impairment in the subject.

Preferably, according to this embodiment, the NGF is administered to the subject starting between 6 hours and 15 days after birth, preferably starting between 24 hours and 7 days after birth.

Also disclosed herein are methods of preventing and/or treating motor impairment associated with (e.g., affected or caused by) neonatal hypoxic-ischemic encephalopathy in a subject in need thereof, the method comprising administering a therapeutically effective amount of nerve growth factor (NGF) intranasally to the subject.

This method involves the delivery of NGF to the subject to promote the survival, growth, and repair of motor neurons, thereby enhancing motor function and reducing motor deficits. In some instances, the intranasal delivery allows for efficient transport across the blood-brain barrier and targeted action within the central nervous system. By stimulating neuroplasticity, synaptic regeneration, and the reestablishment of motor pathways, NGF administration can improve motor coordination, strength, and overall mobility in subjects with motor dysfunction. The method can involve periodic cycles of NGF administration to maximize therapeutic effects, and the treatment is designed to restore motor capabilities, enhance the quality of life, and slow the progression of motor impairment over time.

The motor impairment caused by neonatal hypoxic-ischemic encephalopathy can result from muscle tone deregulation. This deregulation can affect the movement and coordination of the affected individual. By administering NGF, it is possible to address these motor deficits and improve overall motor function in the subject. The treatment specifically targets the underlying neurological mechanisms that contribute to motor dysfunction.

In particular, administering NGF as described in this method can help normalize the muscle tone of a subject suffering from neonatal hypoxic-ischemic encephalopathy. By targeting the underlying neurological dysfunction that causes muscle tone abnormalities, NGF can restore more normal motor function, thereby improving the subject's quality of life and ability to perform daily activities.

The muscle tone deregulation that results from neonatal hypoxic-ischemic encephalopathy can be associated with conditions such as cerebral palsy. Cerebral palsy is a group of disorders that affect movement and muscle tone, often caused by brain damage or abnormal brain development. The treatment outlined in the present disclosure offers a potential therapeutic intervention for subjects suffering from this debilitating condition.

The muscle tone deregulation can manifest in a variety of ways, including hypotonia, flaccidity, hypertonia, dystonia, ataxia, extrapyramidal symptoms, diplegia, tetraplegia, quadriplegia, hemiplegia, and paraplegia. Each of these conditions presents unique challenges in terms of motor control and function, making the use of NGF as a treatment for such disorders highly beneficial. The ability to address various forms of muscle tone deregulation broadens the scope of this method.

More specifically, hypotonia, which refers to low muscle tone, can be either focal or generalized. Focal hypotonia affects specific muscle groups, while general hypotonia affects the entire body. Both types of hypotonia can impair motor function and lead to difficulty with movement, balance, and coordination. NGF administration can help normalize muscle tone and improve overall motor performance in subjects affected by these conditions.

Similarly, dystonia, a condition characterized by involuntary muscle contractions that cause twisting and abnormal postures, can also be treated with NGF. Dystonia can present as focal dystonia, affecting a specific part of the body, segmental dystonia, affecting multiple regions, or general dystonia, which involves widespread muscle involvement. NGF has the potential to alleviate the symptoms of these types of dystonia and restore more functional muscle control.

Hypertonia, or increased muscle tone, is another condition that can result from neonatal hypoxic-ischemic encephalopathy. This can include spasticity, rigidity, and paratonia, which can cause muscle stiffness and resistance to movement. NGF treatment can help reduce these symptoms by regulating the neural circuits involved in muscle tone, thus improving motor control and functionality.

A further object of the disclosure is nerve growth factor (NGF) for use in the prevention and/or treatment of cerebral palsy (CP) associated with (e.g. affected or caused by) neonatal hypoxic-ischemic encephalopathy (HIE) or a clinical manifestation thereof in a subject, wherein said NGF is administered intranasally to the subject.

In some instances, the present disclosure relates to NGF for use in curing cerebral palsy (CP) associated with (e.g. affected or caused by) neonatal hypoxic-ischemic encephalopathy (HIE) or a clinical manifestation thereof in a subject, wherein said NGF is administered intranasally to the subject.

In some instances, the present disclosure relates to NGF for use in slowing down cerebral palsy (CP) associated with (e.g. affected or caused by) neonatal hypoxic-ischemic encephalopathy (HIE) or a clinical manifestation thereof in a subject, wherein said NGF is administered intranasally to the subject.

In some instances, the present disclosure relates to NGF for use in lessening the severity of cerebral palsy (CP) associated with (e.g. affected or caused by) neonatal hypoxic-ischemic encephalopathy (HIE) or a clinical manifestation thereof in a subject, wherein said NGF is administered intranasally to the subject.

In some instances, the present disclosure relates to NGF for use in halting the progression of cerebral palsy (CP) associated with (e.g. affected or caused by) neonatal hypoxic-ischemic encephalopathy (HIE) or of a clinical manifestation thereof in a subject, wherein said NGF is administered intranasally to the subject.

In some instances, the present disclosure relates to NGF for use in slowing the development of cerebral palsy (CP) associated with (e.g. affected or caused by) neonatal hypoxic-ischemic encephalopathy (HIE) or of a clinical manifestation thereof in a subject, wherein said NGF is administered intranasally to the subject.

In some instances, the present disclosure relates to NGF for use in reducing the likelihood of occurrence of cerebral palsy (CP) associated with (e.g. affected or caused by) neonatal hypoxic-ischemic encephalopathy (HIE) or of a clinical manifestation thereof in a subject, wherein said NGF is administered intranasally to the subject.

In some instances, the present disclosure relates to NGF for use in reducing the severity of occurrence of cerebral palsy (CP) associated with (e.g. affected or caused by) neonatal hypoxic-ischemic encephalopathy (HIE) or of a clinical manifestation thereof in a subject, wherein said NGF is administered intranasally to the subject.

In some instances, the subject is a human subject, preferably a neonate or an infant.

In some instances, said clinical manifestation is selected from motor impairment and cognitive impairment.

In some instances, said motor impairment is as described above.

In some instances, said subject has been diagnosed with cerebral palsy associated with (e.g. affected or caused by) neonatal hypoxic-ischemic encephalopathy and said NGF is for use in the treatment of said cerebral palsy in said subject, by intranasal administration to said subject.

Said treatment can include one or more of the following: curing, slowing down, lessening the severity of, halting the progression of cerebral palsy in said subject.

In some instances, said subject has been identified as being at risk of developing cerebral palsy associated with (e.g. affected or caused by) neonatal hypoxic-ischemic encephalopathy and said NGF is for use in the prevention of said cerebral palsy in said subject, by intranasal administration to said subject.

Said prevention can include one or more of the following: reducing the likelihood of occurrence, reducing the likelihood of severity, slowing the development of cerebral palsy in said subject.

In some instances, the present disclosure provides a method for preventing and/or treating cerebral palsy (CP) associated with (e.g. affected or caused by) neonatal hypoxic-ischemic encephalopathy in a subject through the intranasal administration of nerve growth factor (NGF) (e.g., SEQ ID NO:1 or any NGF composition described herein). The method involves the administration of NGF to a subject diagnosed with CP, with the aim of promoting neuronal survival, enhancing synaptic plasticity, and restoring neurovascular function in the affected regions of the brain. NGF is administered intranasally to ensure efficient delivery to the central nervous system while minimizing systemic exposure. The treatment is designed to target the motor and cognitive impairments commonly associated with CP, by promoting the repair of damaged neural pathways, enhancing neurotrophic support to the surviving neurons, and stimulating the growth of new synaptic connections. NGF administration is carried out over a specified duration, with a preferred treatment regimen involving intermittent cycles of administration to optimize therapeutic effects while minimizing potential side effects. The method offers a promising approach to improving both motor function and quality of life for individuals with CP, by enhancing brain plasticity and fostering long-term neurorestorative effects.

A further object of the present invention is nerve growth factor (NGF) for use in promoting neurodevelopment in a subject diagnosed with neonatal hypoxic-ischemic encephalopathy (HIE), wherein said NGF is administered intranasally to the subject.

In some instances, promoting neurodevelopment includes enhancing neuronal survival, synaptic formation, and/or the establishment of neural networks necessary for proper cognitive, motor, and sensory function.

In some instances, the present disclosure provides a method for promoting neurodevelopment in a subject diagnosed with neonatal hypoxic-ischemic encephalopathy through the intranasal administration of nerve growth factor (NGF). This method involves the delivery of NGF to the subject to stimulate the growth, differentiation, and maturation of neurons, thereby supporting healthy brain development. NGF is administered via intranasal delivery, which allows for efficient transport across the blood-brain barrier and direct action on the central nervous system. The treatment is particularly beneficial during critical periods of brain development, where NGF enhances neuronal survival, synaptic formation, and the establishment of neural networks necessary for proper cognitive, motor, and sensory function. The method is designed to address neurodevelopmental disorders resulting from NHIE, by promoting neurotrophic support to developing neurons and stimulating brain plasticity. The administration regimen can include periodic cycles of NGF treatment to optimize its neuroprotective and neuroregenerative effects, ultimately supporting healthier neurodevelopment and improving long-term neurological outcomes.

"Neurodevelopment" refers to the process by which the nervous system, including the brain and spinal cord, matures and organizes throughout prenatal, neonatal, and early postnatal stages of life. This process encompasses the growth, differentiation, migration, and maturation of neurons, as well as the formation of synaptic connections and neural networks necessary for the establishment of cognitive, motor, sensory, and emotional functions. Neurodevelopment is a highly dynamic and sensitive process that occurs during critical windows of development and is influenced by genetic, environmental, and physiological factors. Disruptions in neurodevelopment can lead to a variety of neurological and neuropsychiatric disorders, including developmental delays, intellectual disabilities, autism spectrum disorders, and other neurodevelopmental disorders. The proper progression of neurodevelopment is essential for the establishment of functional brain circuits and the overall well-being and function of an individual's nervous system.

In some instances, the neonatal hypoxic-ischemic encephalopathy (HIE) is selected from mild neonatal hypoxic-ischemic encephalopathy (HIE) (stage 1), moderate neonatal hypoxic-ischemic encephalopathy (HIE) (stage 2) and severe neonatal hypoxic-ischemic encephalopathy (HIE) (stage 3) as determined according to the staging system developed by Sarnat and Sarnat (Sarnat H B, Sarnat M S. Arch Neurol 1976; 33: 696-705).

In some instances, the neonatal hypoxic-ischemic encephalopathy (HIE) is moderate neonatal hypoxic-ischemic encephalopathy (HIE) or severe neonatal hypoxic-ischemic encephalopathy (HIE).

In some instances, the subject is a neonate or an infant.

In some instances, the subject has a gestational age at birth of at least 36 weeks.

In some instances, the subject weighs at least 1800 grams at birth.

In some instances, the subject has at least one of the following signs of perinatal depression:

Apgar score less than 5 at 10 minutes of age, need for resuscitation (e.g., chest compressions, mechanical ventilation, or CPAP) at 10 minutes of age, pH less than 7.00 in a cord blood gas, or in a neonate blood gas obtained at a time less than 60 minutes of age, base deficit $\geq 12$ mmol/L, or $\geq 15$ mmol/L, or $\geq 16$ mmol/L in a cord (arterial or venous) gas, or in an infant gas (arterial or venous) obtained at a time less than 60 minutes of age.

In some instances, the subject has been treated with therapeutic hypothermia started prior to 6 hours after birth.

In some instances, the NGF for use according to the present disclosure is administered to the subject for the first time within one month after birth (e.g., 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days), preferably within seven days after birth, more preferably within 72 hours after birth (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours), more preferably within 36 hours after birth, and even more preferably within 24 hours after birth.

In some instances, the NGF for use according to the present disclosure is administered to the subject for the first time at one month or later after birth, preferably between one month and 36 months after birth, more preferably between one month and 24 months after birth, more preferably between one month and 12 months after birth, even more preferably between one month and six months after birth, and most preferably between one month and four months after birth.

In some instances, the NGF for use according to the present disclosure is administered to the subject for the first time between three to nine months after birth, preferably between three to six months after birth.

In some instances, the NGF for use according to the disclosure is administered to the subject daily or every two/three days throughout the period of treatment.

In some instances, the period of treatment is a period between 7 and 90 days. In some instances the period of treatment is between 15 and 60 days.

In some instances, the NGF for use according to the disclosure is administered to the subject from one to three times a day.

In some instances, the administration schedule is a continuous administration schedule, wherein the NGF is administered according to the same schedule for the period of treatment.

Alternatively, several cycles of treatment can be performed.

In some instances, the administration schedule is an intermittent administration schedule, with two or more cycles of periods of treatment alternated by wash-out periods.

In some instances, the NGF for use according to the present disclosure is administered to the subject for at least three cycles, wherein each cycle comprises seven days of daily intranasal administration of NGF followed by 21 days of washout (i.e., a period wherein NGF is not administered to the subject).

The effective amount of the NGF used in each administration, the duration of the treatment and the number of administrations per day are selected by the skilled person on the basis of the characteristics of the subject to be treated, the severity of the motor impairment or of the other conditions to be prevented or treated and on the basis of assessment tests carried out during the treatment.

In some instances, the total dose of NGF for use according to the present disclosure that is administered to the subject is between 25 µg/kg and 400 µg/kg, preferably between 30 µg/kg and 300 µg/kg, more preferably between 35 µg/kg and 200 µg/kg, more preferably between 40 µg/kg and 100 µg/kg, more preferably between 40 µg/kg and 60 µg/kg, more preferably between 45 µg/kg and 55 µg/kg, even more preferably it is 50 µg/kg.

In some instances, the dose per cycle of NGF for use according to the present disclosure that is administered to the subject is between 15 µg/kg and 20 µg/kg, more preferably between 16 µg/kg and 17 µg/kg, even more preferably between 16.6 µg/kg and 16.8 µg/kg, most preferably it is 16.7 µg/kg.

In some instances, the daily dose of NGF for use according to the present disclosure that is administered to the subject is between 2 µg/kg and 3 µg/kg, preferably between 2.3 µg/kg and 2.5 µg/kg, more preferably it is 2.4 µg/kg.

In some instances, the dose per nostril of NGF for use according to the present disclosure that is administered to the subject is between 0.3 µg/kg/nostril and 1 µg/kg/nostril, more preferably between 0.4 µg/kg/nostril and 0.8 µg/kg/nostril, more preferably between 0.5 µg/kg/nostril and 0.7 µg/kg/nostril, most preferably it is 0.6 µg/kg/nostril.

In some instances, the daily dose of NGF for use according to the present disclosure is administered to the subject twice daily with 12 hours interval.

In some instances, the amount of NGF per each intranasal administration is between about 5 µg and about 1 mg. In some instances, the amount of NGF per each intranasal administration is between about 10 µg and about 400 µg. In some instances, the amount of NGF per each intranasal administration is between about 15 µg and about 200 µg. In some instances, the amount of NGF per each intranasal administration is about 20 µg.

In some instances, prior to NGF treatment, the subject is treated under hypothermic conditions.

The present disclosure provides a method for treating a newborn diagnosed with neonatal hypoxic-ischemic encephalopathy (NHIE) under hypothermic conditions. The method involves administering controlled therapeutic hypothermia to the newborn, wherein the newborn's body temperature is maintained at a lower-than-normal range, typically between 32° C. and 34° C., for a defined period of time, usually 72 hours. This therapeutic hypothermia is initiated as soon as NHIE is diagnosed, typically within the first six hours of life, to mitigate brain injury caused by oxygen deprivation and improve neurological outcomes. The newborn is carefully monitored throughout the treatment, with continuous assessment of core body temperature, neurological function, and vital signs to ensure that hypothermic conditions are maintained safely without causing further harm. During this period, the newborn can be placed in a specialized cooling device or incubator, where the temperature is regulated to provide optimal conditions for neuroprotection. Once the cooling phase is completed, gradual rewarming is conducted to restore the newborn to normothermic conditions. This method effectively reduces the extent of brain damage, enhances recovery, and improves long-term neurological function in infants suffering from NHIE.

In another embodiment, the present disclosure provides for the late therapeutic administration of nerve growth factor (NGF) to a subject for the treatment or prevention of a brain disease. In this approach, NGF is administered starting from one month after birth, with defined therapeutic windows extending up to 36 months postnatally. Preferably, the administration occurs between one month and 24 months after birth, more preferably between one month and 12 months after birth, even more preferably between one month and six months after birth, and most preferably between one month and four months after birth. The administration of NGF during this period aims to support ongoing neuronal maturation, synaptic connectivity, and neuroplasticity, which remain critical beyond the neonatal stage. By delivering NGF within these timeframes, the treatment can mitigate progressive neuronal damage, enhance cognitive and motor function, and improve long-term neurological outcomes.

In another embodiment, the present disclosure describes the administration of nerve growth factor (NGF) within a defined postnatal window ranging from three months to nine months after birth, with a preferred timeframe of three to six months after birth.

In some instances, the NGF is human NGF.

In some instances, the human NGF has the amino acid sequence of SEQ ID NO:1 below

```
SEQ. ID NO: 1:
SSSHPIFHRGEFSVCDSVSVWVGDKTTATDIKGKEVMVLGEVNINNSVF
KQYFFETKCRDPNPVDSGCRGIDSKHWNSYCTTTHTFVKALTMDGKQA
AWRFIRIDTACVCVLSRKAVR
```

Alternatively, the human NGF has the amino acid sequence of SEQ ID NO:2 below:

```
SEQ ID NO: 2:
SSSHPIFHRGEFSVCDSVSVWVGDKTTATDIKGKEVMVLGEVNINNSVF
KQYFFETKCRDPNPVDSGCRGIDSKHWNSYCTTTHTFVKALTMDGKQA
AWRFIRIDTACVCVLSRKAVRRA
```

Alternatively, the human NGF is a mixture of NGFs having sequences of SEQ ID NO: 1 and SEQ ID NO:2.

The human NGF of SEQ ID NO:2 has an amino acid sequence that only differs from the NGF of SEQ ID NO: 1 for the presence of two additional amino acids at the C-terminus. Both forms of NGF are found in human cells and therefore are considered as wild type human NGF.

Therefore, when referring to "human NGF" or "wild type human NGF" in the present application, it is meant a human NGF of SEQ ID NO:1 or of SEQ ID NO:2.

In some instances, the NGF is produced by recombinant DNA technology. In some instances, the NGF is a human recombinant NGF (rhNGF). Methods of producing rhNGF are known to the person skilled in the art, for example those described in WO0022119 A1 and WO2013092776 A1.

In some instances, the NGF has a purity higher than 70%. In some instances, the NGF has a purity higher than 80%, higher than 90%, higher than 95%, higher than 98%, or higher than 99%. The purity of NGF can be determined by conventional means known to those skilled in the art, for example by HPLC analysis. Substantially pure refers to material which is at least 70% pure (i.e., free from contaminants), at least 90% pure, at least 95% pure, at least 98% pure, or at least 99% pure.

A further object of the present disclosure is a pharmaceutical composition for intranasal administration comprising the NGF as described above and at least one pharmaceutically acceptable excipient, for use in the prevention and/or treatment of motor impairment associated with (e.g., affected or caused by) neonatal hypoxic-ischemic encephalopathy (HIE) in a subject, wherein the pharmaceutical composition is administered intranasally to the subject.

In some instances, the motor impairment is as described above.

A further object of the present disclosure is a pharmaceutical composition for intranasal administration comprising the NGF as described above and at least one pharmaceutically acceptable excipient, for use in the prevention and/or treatment of cerebral palsy (CP) associated with (e.g., affected or caused by) neonatal hypoxic-ischemic encephalopathy (HIE) in a subject, wherein the pharmaceutical composition is administered intranasally to the subject.

In some instances, the cerebral palsy (CP) is as described above.

A further object of the present disclosure is a pharmaceutical composition for intranasal administration comprising the NGF as described above and at least one pharmaceutically acceptable excipient, for use in the prevention and/or treatment of neurodevelopmental disability associated with (e.g., affected or caused by) neonatal hypoxic-ischemic encephalopathy (HIE) in a subject, wherein the pharmaceutical composition is administered intranasally to the subject.

In some instances, the neurodevelopmental disability is as described above.

A further object of the present disclosure is a pharmaceutical composition for intranasal administration comprising the NGF as described above and at least one pharmaceutically acceptable excipient, for use in promoting neurodevelopment in a subject affected by neonatal hypoxic-ischemic encephalopathy (HIE) in a subject, wherein the pharmaceutical composition is administered intranasally to the subject.

In some instances, said neurodevelopment is as described above.

In some instances, the pharmaceutical composition for use according to the disclosure is a liquid intranasal composition.

In some instances, the pharmaceutical composition for use according to the disclosure comprises an effective amount of the NGF as described above and at least one pharmaceutically acceptable excipient suitable for intranasal use. In some instances, the pharmaceutically acceptable excipient is selected from solvents, thickening agents, mucoadhesive agents, buffers, antioxidants, surfactants, preservatives, and penetration enhancers.

In some instances, the concentration of the NGF in the liquid intranasal composition for use according to the disclosure is between about 5 µg/ml and about 1 mg/ml. In some instances, the concentration of the NGF in the liquid intranasal composition for use according to the disclosure is between about 10 µg/ml and about 400 µg/ml. In some instances, the concentration of the NGF in the liquid intranasal composition for use according to the disclosure is between about 15 µg/ml and about 200 µg/ml. In some instances, the concentration of the NGF in the liquid intranasal composition for use according to the disclosure is about 20 µg/ml.

In some instances, the solvent is water.

In some instances, the mucoadhesive agent is glycerol. In some instances, the mucoadhesive agent (e.g., glycerol) is at a concentration between 0.05% w/v and 0.2% w/v. In some instances, the mucoadhesive agent (e.g., glycerol) is at a concentration of 0.1% w/v.

In some instances, the antioxidant is methionine. In some instances, the antioxidant (e.g., methionine) is at a concentration between about 0.005 mg/ml and about 0.02 mg/ml. In some instances, the antioxidant (e.g., methionine) is about 0.01 mg/ml.

In some instances, the surfactant is Kolliphor P188. In some instances, the surfactant (e.g., Kolliphor P188) is at a concentration between about 0.05% w/v and about 0.2% w/v. In some instances, the surfactant (e.g., Kolliphor P188) is about 0.1% w/v.

In some instances, the buffer is phosphate buffer.

In some instances, the penetration enhancer is n-Dodecyl-β-D-maltoside. In some instances, the penetration enhancer (e.g., n-Dodecyl-β-D-maltoside) is at a concentration between about 0.1% w/v and about 1% w/v. In some instances, the penetration enhancer (e.g., n-Dodecyl-β-D-maltoside) is about 0.5% w/v.

In some instances, the liquid intranasal composition for use according to the disclosure comprises or consists of the NGF as described above, sodium chloride, phosphate buffer, and water.

In some instances, the liquid intranasal composition for use according to the disclosure comprises or consists of the NGF as described above, sodium chloride, phosphate buffer, Kolliphor P188, L-Methionine, and water.

In some instances, the liquid intranasal composition for use according to the disclosure comprises or consists of the NGF as described above, sodium chloride, phosphate buffer, Kolliphor P188, L-Methionine, Glycerol, n-Dodecyl-β-D-maltoside and water.

In some instances, the liquid intranasal composition for use according to the disclosure comprises or consists of NGF, NaH2 PO4*H2O, NaCl, Kolliphor P188, -L-Methionine. In some instances, the liquid intranasal composition includes n-Dodecyl-β-D-maltoside. In some instances, the liquid intranasal composition includes glycerol. In some instances, the liquid intranasal composition includes water.

In some instances, the liquid intranasal composition for use according to the disclosure comprises or consists of the following components:

NGF as described above, at a concentration:
    between about 5 µg/ml and about 1 mg/ml,
    between about 10 µg/ml and about 400 µg/ml, or
    between about 15 µg/ml and about 200 µg/ml,
NaH2 PO4*H2 O, at a concentration:
    between about 5 and about 8 mg/ml, or
    at about 6.9 mg/mL, NaCl, at a concentration:
  between about 5 and about 6.5 mg/ml, or
  about 5.84 mg/mL,
Kolliphor P188, at a concentration:
  between about 0.05% w/v and about 0.2% w/v, or
  about 0.1% w/v,
L-Methionine, at a concentration:
  between about 0.05 mg/ml and about 0.2 mg/ml, or
  about 0.1 mg/ml,
Optionally, n-Dodecyl-β-D-maltoside, at a concentration:
  between about 0.1% w/v and about 1% w/v, or
  about 0.5% w/v,
  and/or
glycerol, at a concentration:
  between about 0.05% w/v and about 0.2% w/v, or
  about 0.1% w/v, and
Water.

The pharmaceutical composition for use according to the disclosure can be suitably formulated using appropriate methods known in the art or by the method disclosed in Remington's Pharmaceutical Science (recent edition), Mack Publishing Company, Easton Pa.

In some instances, the NGF used in the method of the disclosure is in form of a pharmaceutical composition, as above described.

The disclosure will be further described in the following examples, which do not limit the scope of the disclosure described in the claims.

EXAMPLES

Example 1

The biodistribution of NGF in rat brain areas after single intranasal administration was evaluated.

A formulation containing 1.2 mg/ml of rhNGF (i.e., comprising SEQ ID NO:1) was administered once intranasally to rats.

Rats were sacrificed at different time-points corresponding to 2 hours, 4 hours, 8 hours and 24 hours after treatment. Samples from parietal cortex, hypothalamus, thalamus, striatum, hippocampus, brainstem, frontal cortex and medial septum were collected for rhNGF quantitative determination by ELISA and cumulative absorption (2-24 hours) was calculated. Before analysis, brain samples were homogenized in ice by ultraturrax and centrifuged for supernatants recovery. A commercial ELISA kit (RayBiotech, Catalogue ELH-BNGF) was used according to the instructions provided by the supplier. The calibration curve range for NGF determination was established at 20.5-5000 pg/mL.

As shown in FIG. 1, NGF absorption was evident in all brain tissues, but the protein particularly concentrates in areas involved in motor activity, especially in hypothalamus and thalamus.

Example 2

The effect of NGF on motor impairment associated with neonatal hypoxic-ischemic encephalopathy was evaluated in a mouse model representative of this condition. The ipsilateral ischemic injury was induced according to Rice-Vannucci model, with few modifications (Rice et al., Ann. Neurol., 9 (1981), pp. 131-141; R. C. Vannucci et al., J. Cerebr. Blood Flow Metabol., 24 (2004), pp. 1090-1097; S. J. Vannucci and H. Hagberg, J. Exp. Biol., 207 (2004), pp. 3149-3154; Xu et al., Mol. Neurobiol., 53 (2016), pp. 5962-5970).

In particular, C57 BL/6 mice (postnatal day 7) were anesthetized with 1.5% sevoflurane, and 98.5% O2 (Oxygen concentrator, Mod. LFY-I-5). The body temperature of the animal was maintained at 37±0.5° C. during the whole procedure with a heating pad. Under a surgical stereomicroscope, a midline skin incision (0.5 cm) was made on the neck, and the right common carotid artery (CCA) was exposed and double ligated with a suture thread (6-0), in order to isolate the region respectively upstream and downstream of the area to be cut. CCA was cut between the two knots by using specific micro-clipper. The incision was rinsed with 1% lidocaine and sutured with a 6.0 polypropylene (Prolene) suture. Animals were returned to their dams and monitored continuously during a recovery period of 1 h. After that, the pups were subjected to hypoxia (60 min) induced by placing animals into a hypoxic chamber, perfused with an equilibrated gaseous mixture (8% O2 and 92% N2) which composition was monitored by using an oxygen monitor. The hypoxic chamber was placed in a water bath heated to 37° C. At the end of the procedure, pups were returned to their dams. Animals were monitored continuously for 30 min and then checked every 30 min for 2 h and then daily until they were sacrificed.

Motor Performance Test

The following tests were carried out in order to evaluate the motor performance of the animals: wire hanging test, rotarod test and beam walking test.

Wire Hanging Test

The wire hanging test examines the forelimb motor strength of mice (Crawley, J. N. What's Wrong with My Mouse: Behavioral Phenotyping of Transgenic and Knockout Mice. 2 nd edn, Wiley-Interscience, 2007). In this test, the mice were trained to suspend their bodies from a steel wire (2 mm in diameter) with only their forelimbs (SansBio, China). The wire was held with two posts 40 cm above a soft pillow (Dirnagl, U. 2010, Royl, G. 2009, Brain Res. 1265, 148-157) The mice were trained for 2 days with 3 trials per day, starting from postnatal day 21 (P21) to P28. The time until the mouse fell (holding time) was recorded and the averages of three trials were further analyzed.

Beam Walking Test

Sensory-motor coordination was tested using balance beams (45 cm length; 30% incline). Each mouse was given three trials per beam for 2 days a week, starting from postnatal day 21 (P21) to P28. Latency to traverse the beam was scored and averaged. Failure to traverse the beam during the allotted time terminated the trial and the maximum time (180 s) was measured (Anzilotti et al., Cell Death Dis., 2015 Dec. 3; 6(12):e2004).

Rotarod Test

Each mouse was given three trials per rotarod for 2 days a week, starting from postnatal day 21 (P21) to P28. Motor coordination and balance were assessed using a five-station mouse rotarod apparatus (Ugo Basile; Milan, Italy). In each station, the rod was 6 cm in length and 3 cm in diameter. Mice were trained to maintain balance at increasing speed up to a constant speed of 14 rpm for three consecutive trials. The test sessions were conducted by one rotarod trial administered once a week. In this session, the speed of rotation was increased from 4 to 14 rpm over 60 s. The maximum latency of 60 s was assigned to the mice that did not fall at all (Giampa et al., PLOS One, 2010 Oct. 15; 5(10):e13417).

Drugs Administration

Mice were daily treated with vehicle or with rhNGF (50 µg/Kg) (i.e., comprising SEQ ID NO: 1) administered by intranasal route for 3 weeks starting at 7 hours from HI induction. The intranasal administration was carried out as follows.

Using a dominant hand, the micropipette P-20 was loaded with 10 µl of compound or vehicle. The tip of the filled pipette was placed near the mouse's left nostril at 45-degree angle. The drop was placed close enough to the mouse's nostril, both left and right, so that the mouse could inhale the drop. Immediately after the mouse inhaled this small drop, the rest of the compound in the pipette tip was expelled to form another small drop that the mouse inhaled through the same nostril about 2-3 seconds later. After administration, the mouse was held in this position for 15 sec.

Study Design

Behavioral evaluations were performed at 28-30 days postnatal.

Animals were divided in the following groups:

$Sham$/Vehicle ($n = 10$)

$Sham + rhNGF$ ($50\,\mu g$/Kg) ($n = 10$)

$HI +$ Vehicle ($n = 10$)

$HI + rhNGF$ ($50\,\mu g$/Kg) ($n = 10$)

Figure 2:
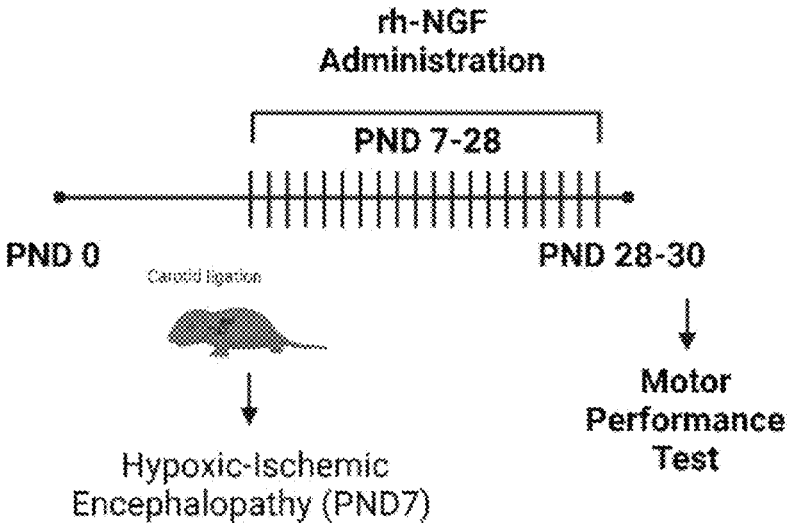
FIG. 2 shows the experimental timeline of the study described in Example 2.

Intranasal intermittent delivery of rh-NGF (50 ug/kg administration for 21 days), was started 7 hours post-HI, when secondary energy failure started (Tetorou K et al., Front Synaptic Neurosci. 2021 Aug. 24; 13:709301), and continued for the following 3 weeks, as shown in FIG. 2.

Data were analyzed using GraphPad Prism version 8.04 (GraphPad Software). Data from behavioral experiments were expressed as mean±SEM. One-way ANOVA followed by Tukey's post hoc tests was used to analyze differences between groups, using treatment (drugs or Vehicle), as factors in the analysis.

Results

Figure 3:
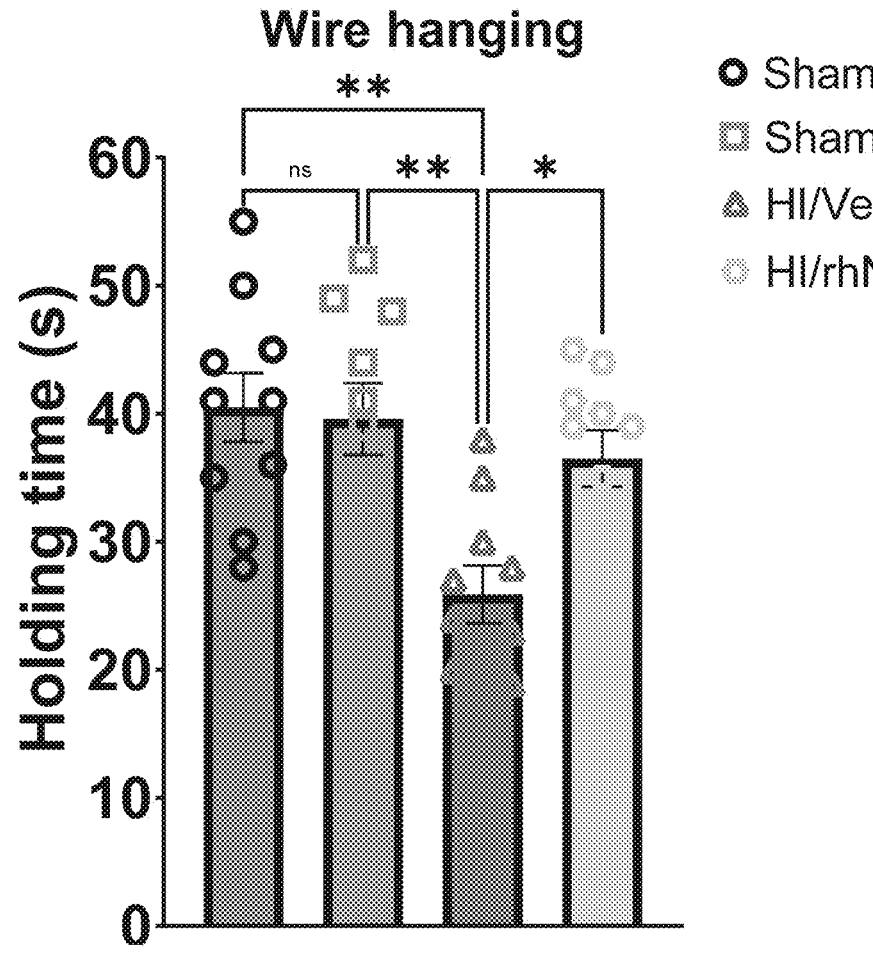
FIG. 3 shows the holding time of sham and hypoxic-ischemic (HI) mice treated with vehicle or with rhNGF in the wire hanging test at 28 days postnatal. N=10 mice per group. Data are shown as the mean and SEM for each group. *One-way ANOVA followed by Tukey's comparison test.

In the wire hanging test, the mice were trained to suspend their bodies from a wire with only their forelimbs. One-way ANOVA analysis showed that the HI condition had significant effects on the holding time of mice (F (3, 36)=7.16, P=0.0007) (FIG. 3). The holding time of the HI mice (25.9±2.27 s) was significantly shorter than that of sham mice (40.5±2.68 s) at 28 days postnatal, suggesting the reduced grip strength of the HI mice (p=0.0012) (FIG. 3). Intriguingly, daily intranasal treatment with rhNGF for 3 weeks, starting 7 hours post-HI, showed a significant rescue of muscular strength. Indeed, HI/rhNGF mice showed a holding time of 36.5±2.21 s (p=0.0024) as compared to HI mice treated with vehicle (FIG. 3). On the contrary, the same treatment did not affect the holding time in Sham mice (39.6±2.79 s; p=0.99) (FIG. 3).

Figure 4:
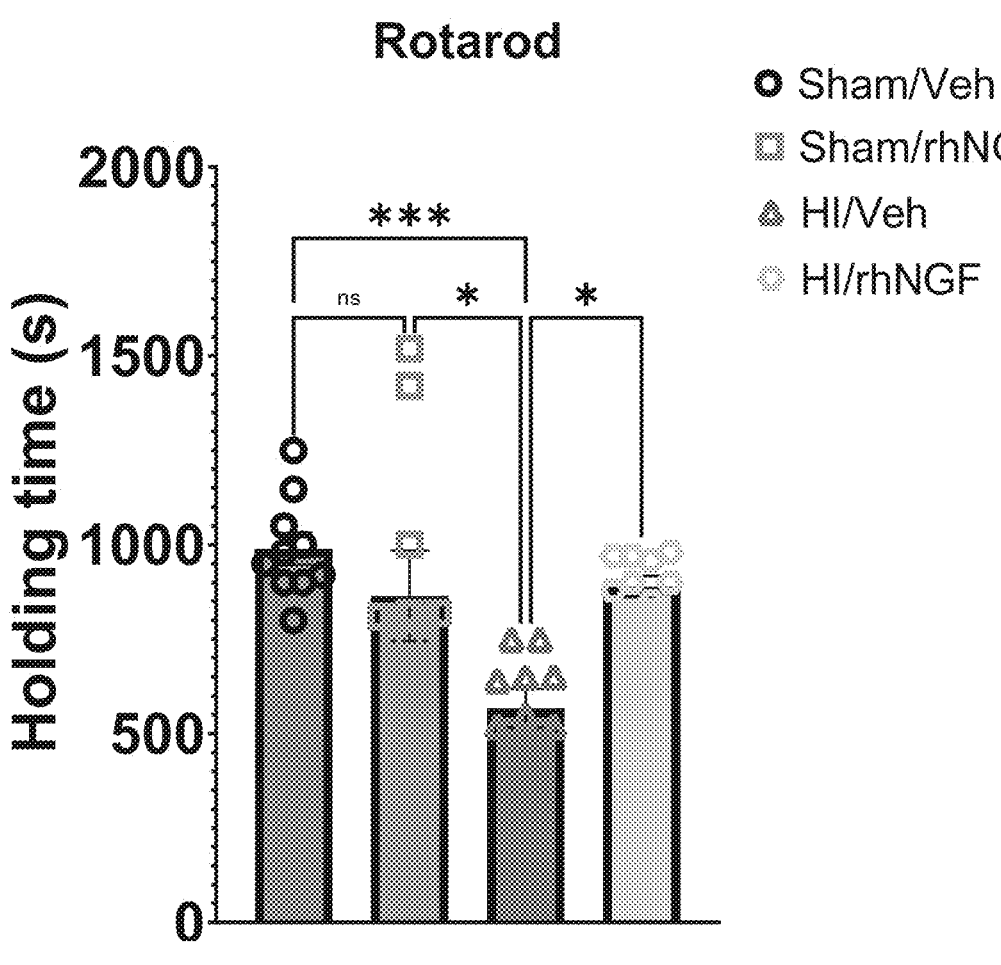
FIG. 4 shows the holding time of sham and HI mice treated with vehicle or with rhNGF in the rotarod test on day 29 postnatal. N=10 mice. Data are shown as the mean and SEM for each group. *One-way ANOVA followed by Tukey's comparison test.

The rotarod test is commonly used to measure the motor coordination and balance of the mice (Crawley, J. N., What's Wrong with My Mouse: Behavioral Phenotyping of Transgenic and Knockout Mice. 2 nd edn, Wiley-Interscience, 2007). In the Rotarod, the mice were trained to suspend their bodies from a wire with only their forelimbs at 29 days postnatal, the sham mice were able to consistently walk on a rotating rod and rarely fell after successive training. One-way ANOVA analysis showed that the HI condition had significant effects on the holding time of mice (F (3, 36)=7.71, P=0.0004). Indeed, quantitative measurements showed that the holding time of the sham mice was 989.7±41.47 s as compared to HI groups that showed a significant lower holding time (567.3±51.03 s, p=0.014) (FIG. 4). As observed in wire hanging test, daily intranasal treatment with rhNGF for 3 weeks, starting 7 hours post-HI, induced a significant increase of holding time on the wheels in HI mice. Indeed, HI/rhNGF mice showed a holding time of 889.8±27.79 s (p=0.011) as compared to HI mice treated with vehicle (FIG. 4). On the contrary, the same treatment did not affect the holding time on the wheels in Sham mice (865±119.26 s; p=0.63) (FIG. 4).

Figure 5:
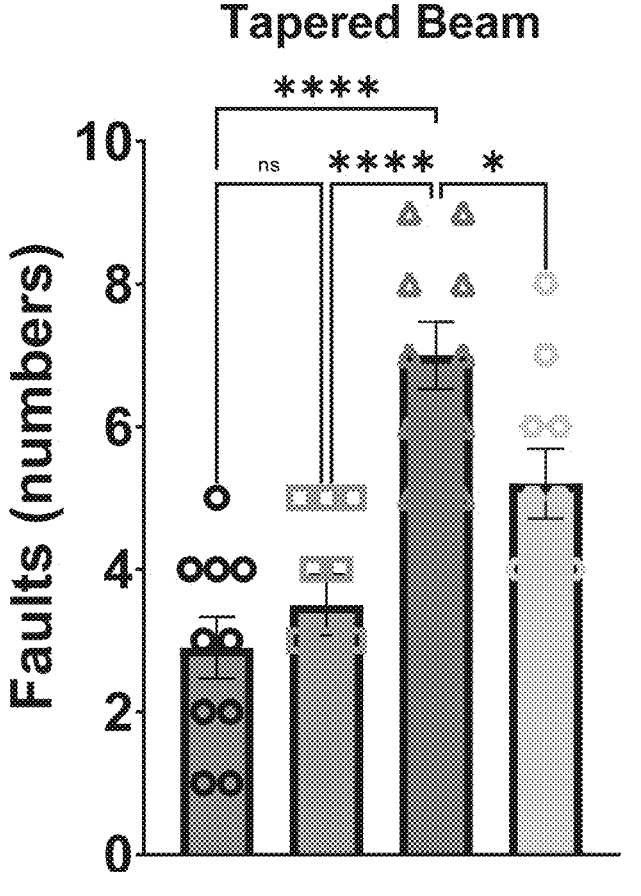
FIG. 5 shows fault numbers of HI and Sham mice treated with vehicle or with rhNGF in tapered beam test at 30 days postnatal. N=10 mice per group. Data are shown as the mean and SEM for each group. *One-way ANOVA followed by Tukey's comparison test.

The tapered beam test is commonly used to evaluate motor dysfunction in a mouse's hind legs (Schaar, K. L, et al., Exp Transl Stroke Med. 2010 Jul. 19; 2(1):13). Sham mice used the central board and passed the beam without many errors of stepping on the ledges (fault) (2.9±0.43) (FIG. 5). However, the HI mice showed a consistent increase in the number of foot faults at 30 days postnatal (7±0.47, p<0.0001) (FIG. 5). One-way ANOVA analysis showed that the HI condition had significant effects on the number of faults in HI mice (F (3, 36)=20.68, P<0.0001). Similar to other motor test, daily intranasal treatment with rhNGF for 3 weeks, starting 7 hours post-HI, normalized the number of faults in HI mice (5.2±0.49, p=0.04) as compared to HI mice treated with vehicle (FIG. 5). On the contrary, the same treatment did not affect the number of faults in Sham mice (3.5±0.42; p=0.76) (FIG. 5).

The data disclosed above comprehensively show that the intranasal administration of NGF is able to restore muscle strength, motor coordination and balance in a murine model of motor impairment associated with HIE. Therefore, the above data support the efficacy of the intranasal administration of NGF in the prevention and/or treatment of motor impairment associated with neonatal hypoxic-ischemic encephalopathy.

Example 3

Intranasal Treatment with a Recombinant Human Nerve Growth Factor (rhNGF) in a Preclinical Model of Neonatal Hypoxic-Ischemic Encephalopathy The study disclosed below aims to evaluate the therapeutic efficacy of recombinant human Nerve Growth Factor (rhNGF, cenegermin-bkbj; i.e., comprising SEQ ID NO:1) in a model of neonatal hypoxic-ischemic injury (NHIE) in rodents. The effects of two treatment regimens (early or late) with rhNGF were evaluated. Animals subjected to the NHIE model were monitored longitudinally using a battery of behavioural tests and neuroimaging techniques.

To replicate the consequences of perinatal ischemic injury, study its neurological outcomes, and evaluate the effects of potential pharmacological treatments, the selected animal model involved subjecting 7-day-old rats to unilateral ligation of the common carotid artery, followed by exposure to a hypoxic environment for 3 hours (model of neonatal hypoxic ischemic encephalopathy, NHIE, as disclosed in Carloni et al., Neurobiol Dis. 2006 January; 21 (1):119-26). From a neurodevelopmental perspective, this stage in rats is considered comparable to that of term human neonates.

Methods

Animals

All procedures involving animals were carried out according to approved protocols by the Italian Ministry of Health, authorization number n° 1014/2024-PR. Pups of *Rattus norvegicus* species and Sprague-Dawley strain were used for the experiments discussed below. Pregnant mothers were received at ~15 days of pregnancy. Special care was provided to the mothers before and after delivery, with hosting in Ministry-authorized rooms for breeding. If possible, pups were distributed evenly across mothers. A veterinary monitored the mothers and the pups to identify any signs of distress.

Model of Neonatal Hypoxic Ischemic Encephalopathy (NHIE)

Figure 6:
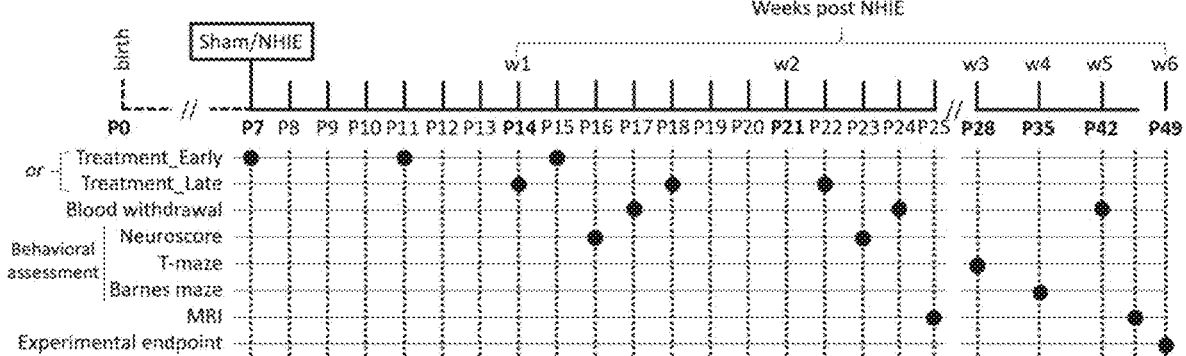
FIG. 6 shows the experimental timeline of the study described in Example 3.

On postnatal day 7 (P7), animals were anaesthetized and surgically prepared to isolate the right carotid artery. The pups underwent ligation of the right common carotid artery, followed by 3 hours of hypoxia in ventilated cages (92% nitrogen and 8% oxygen). Throughout the surgical procedure for ligation, the animals were maintained under deep general anaesthesia, and their body temperature was kept at physiological levels using a feedback-controlled heated pad. Anaesthesia was induced with 3% isoflurane in $O_2/N_2O$ (30:70) and maintained at 1-1.5% isoflurane in $O_2/N_2O$ (30:70). The vascular surgery for ligation of the common carotid artery lasted 10 minutes. The pups were then transferred to the hypoxic chamber for 3 hours, without manipulation. Sham mice received the exposure of the carotid artery, with no ligation nor hypoxic period. At the end of the procedure, the animals were allocated to their specific experimental group (vehicle, early or late hNGF treatment). A schematic of the experimental timeline is shown in FIG. 6.

Early Treatment (Early)

This group of animals received the treatment immediately after hypoxia. The drug (cenegermin-bkbj) was administered intranasally at a dose of 100 μg/kg, evenly split over 3 rounds with 90-minute intervals. The procedure was repeated twice after 3 days of rest from treatment.

Late Treatment (Late)

This group of animals received the same treatment described above, but starting 7 days after NHIE/sham surgery.

Evaluation of Sensorimotor Deficits by the Neuroscore

The evaluation of sensorimotor deficits was done with the neuroscore, as described in Valente A., et al., J Cereb Blood Flow Metab. 2023 July; 43(7):1077-1088. The score ranges from 0 (absence of deficits) to 56 (worst neurological result) and includes general and focal deficits. The general deficits describe the general well-being of the rat with a score between 0 and 28. This score provides information on the physical appearance of the rat, i.e.: fur (0-2), ears (0-2), eyes (0-4), posture (0-4), spontaneous activity (0-4) and presence of epileptic seizures (0-12). Focal deficits describe neurological damage with a score between 0 and 28 and were evaluated through observations on: body symmetry (0-4), gait (0-4), ability to climb a 45° inclined surface (0-4), circling behaviour (0-4), forelimb symmetry (0-4), compulsory circling (0-4) and whisker response (0-4).

Cognitive Deficits

T-Maze: the hippocampal-dependent spatial memory was measured with a standard two arms T-maze apparatus (50× 40×10 cm each arm) in rats on day 28. Animals were tested by an investigator blinded to their identity. Animals were placed into the starting arm of the T-maze and allowed to freely choose to enter one of the two arms in each of the seven trials. A successful alternation consisted of alternate arm entries while unsuccessful alternation occurred when the rat returned to the most recently explored arm. Total arm entries and sequence of entries were recorded for each rat and as percent of correct choice was reckoned, i.e., the number of correct alternations/the maximum number of alternations×100. Rats with intact spatial memory will remember the arm that was previously visited and will prefer to enter a new, unexplored arm (alternation rate ≥60%).

Barnes maze: the test assesses spatial learning and memory, and it was performed on day 28. The maze consists of a circular platform with multiple holes around its perimeter, only one leading to an escape tunnel or a safe area. The test started with a habituation trial (day 1) during which each rat was placed in the centre of the empty arena under a beaker for 30 s, then guided to the escape tunnel over 10-15 s and allowing 2 min to enter the escape tunnel spontaneously. The rat was allowed to stay in the escape for 1 minute and then was taken back to its home cage. In the learning phase (days 2-4), rats were placed for 10 seconds in the centre of the arena and then allowed to explore the arena for at least 2 min to find the escape (primary latency) and to enter it (secondary latency). The test phase (day 5) consisted of the removal of the escape tunnel from the maze to assess the primary latency. The escape was sealed ('false escape') to prevent the rat from falling through the hole. The ability of the rats to find the escape within the 2-minute time was recorded.

Magnetic Resonance Imaging (MRI)

Isoflurane-anesthetized rats (1-1.5% in 30% $O_2$, 70% $N_2O$) were positioned inside the magnet, and both body temperature and respiration were monitored throughout the experiment, allowing for adjustment of the optimal anaesthetic level as needed. MRI acquisitions were then started. At the end of the experiment, animals were removed from the pad and returned to their cage, where they were monitored until they woke up.

Brain imaging was done on a 7 T small-bore animal scanner (BioSpec®; Bruker, Ettlingen, Germany) running ParaVision 6.01 and equipped with a quadrature 1H Cryo-Probe™ (Bruker, Ettlingen, Germany) surface coil as transmitter and receiver. Diffusion tension imaging (DTI) were obtained to quantify white matter (WM) damage.

DTI. echo-planar imaging sequences were acquired (TR/TE=7000/32 ms, resolution 125×125 μm$^2$; FOV 1.5×1.5 cm$^2$; acquisition matrix 120×120, slice thickness 0.3 mm). Diffusion encoding b factors of 800 mm$^2$/s were applied along 19 isotropic directions and two BO unweighted images for each repetition. The diffusion tensor was computed using FSL software. A group mean full tensor template was first created using a population-based DTI atlas construction algorithm that adopts a tensor-based registration procedure embedded in the DTI-TK software library. The average template was then resampled to an in-plane resolution of 100×100 μm$^2$ and slice thickness 0.2 mm, and skeletonized. Fractional anisotropy (FA) images of all subjects were normalized to the mean template with a diffeomorphic transformation and the transformations were applied to all the DTI metrics (MD, RD, AD) which were warped to the mean skeleton for region of interest (ROI)-based analysis. The diffusion tensor was computed using FSL software. A group mean full tensor template was first created with a population-based DTI atlas construction algorithm that uses a tensor-based registration procedure embedded in the DTI-TK software. The average template was resampled to an in-plane resolution of 100·100 lm2 and slice thickness 0.2 mm. A high-resolution FA map of the population-based template was then generated and skeletonized.

The region of interest analyzed was the entire corpus callosum, starting at anteroposteriority +2 mm and ending at −3 mm from the bregma.

Sacrifice

The animals were deeply anaesthetized before sacrifice. The cerebrospinal (CSF) fluid and blood were collected from the cisterna magna and the cava vein, respectively. The CSF was immediately frozen on dry ice. The blood was collected into special tubes washed with EDTA and centrifuged at 2000 rcf for 20 minutes at 4° C. to obtain plasma to be stored in an ultrafreezer at −80° C. until use. Perfusion-fixation or nap-freezing of fresh tissue were done for histological or biochemical analysis, respectively.

Results

Figure 7:
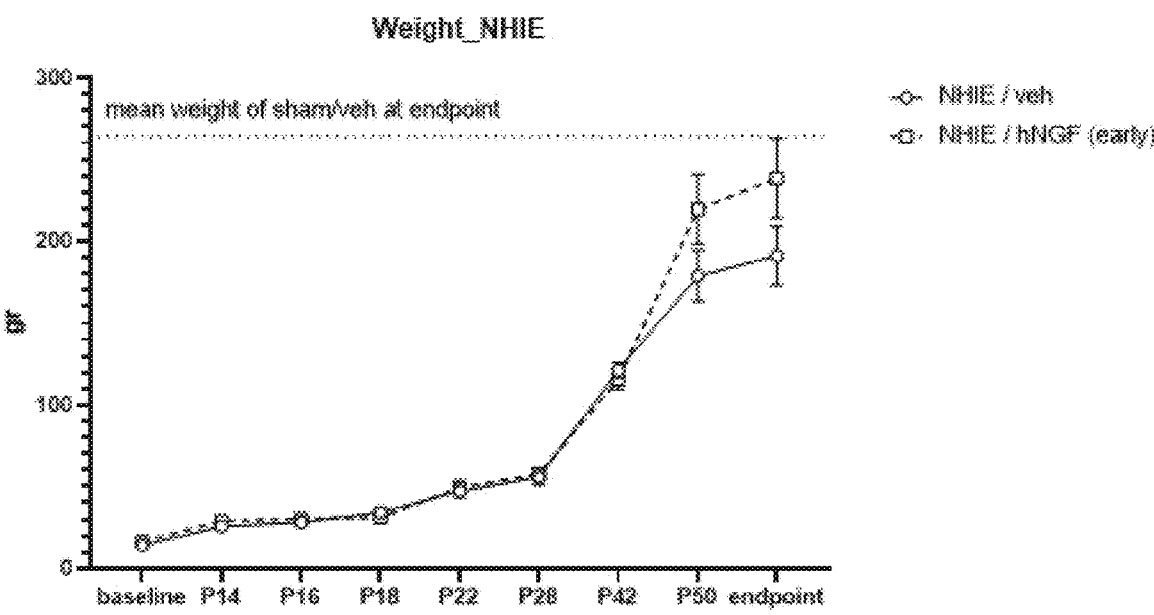
FIG. 7 shows weights of rats in grams from baseline (P7, immediately before surgery) to the endpoint (early treatment).
Figure 8:
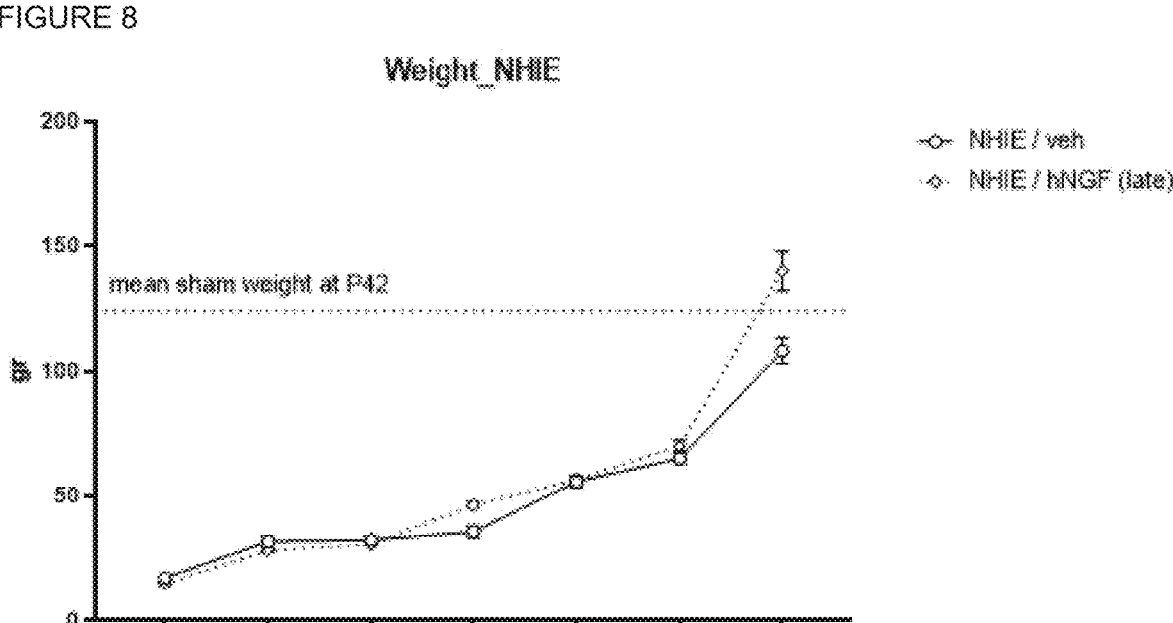
FIG. 8 shows weights of rats in grams from baseline (P7, immediately before surgery) to P42 (late treatment).

Growth curve. Rats receiving hNGF, regardless of the treatment schedule, showed a seemingly steeper growth curve than those receiving vehicle (FIGS. 7 and 8). This is indicative of a trend of attainment at the endpoint of a substantially physiological weight by rats treated with hNGF (both early and late) compared to rats treated with vehicle. Also, while rats treated with hNGF (early) could not reach the same weight of sham animals (FIG. 7), rats treated with hNGF (late) reached and surpassed the weight of sham animals at P42 (FIG. 8). Loss of body weight is indicative of brain injury (Llovera et al., Sci Transl Med. 2015 Aug. 5; 7(299):299 ra121). Thus, these results indicates that rats treated with NGF have less brain injury than rats treated with vehicle and that there is a restoration of general health status comparable to that of sham animals.

Figure 9:
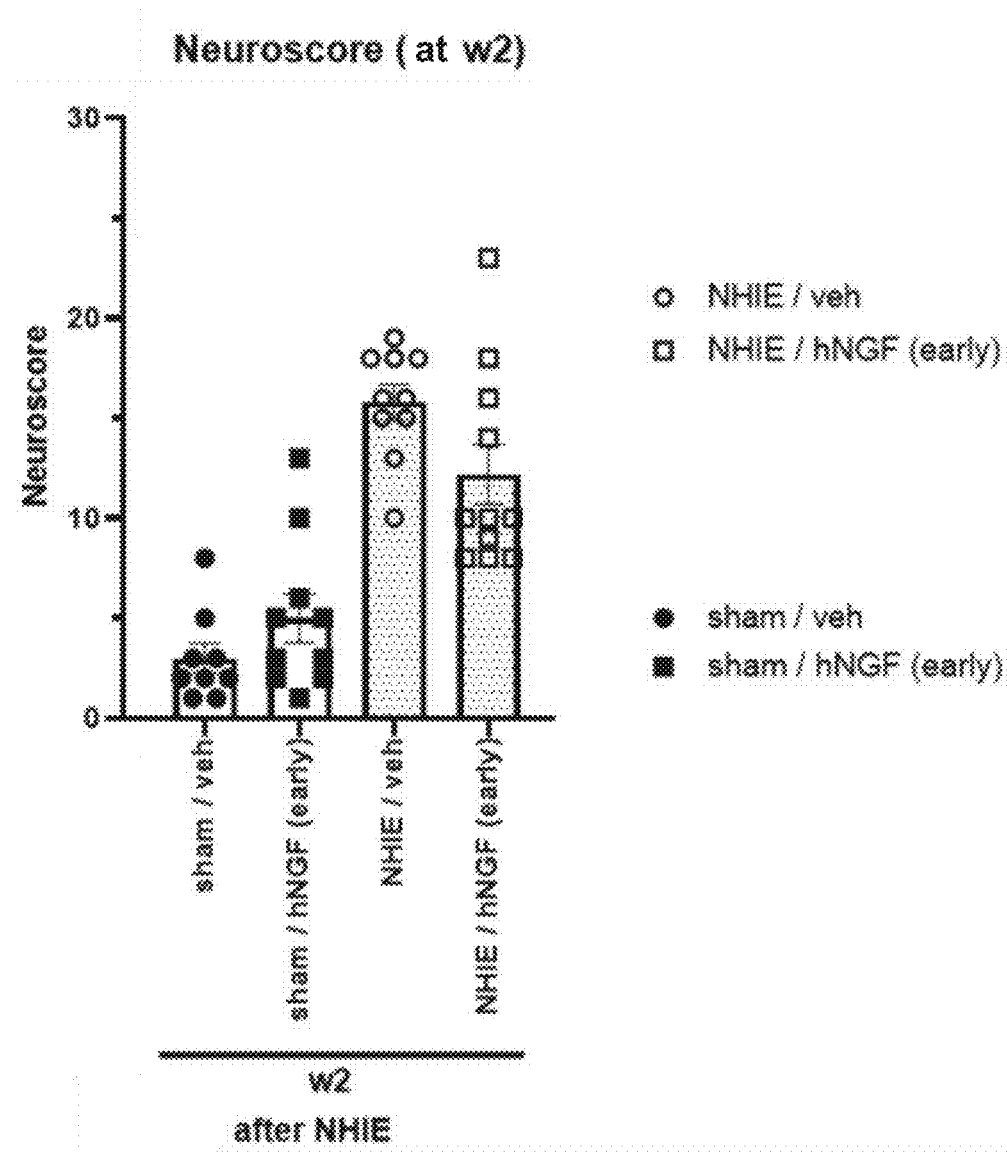
FIG. 9 shows the neuroscore of sham animal (treated with vehicle or with hNGF early) and NHIE animals (treated with vehicle or hNGF early) 2 weeks after induction of NHIE. The higher the score, the worse the outcome.
Figure 10:
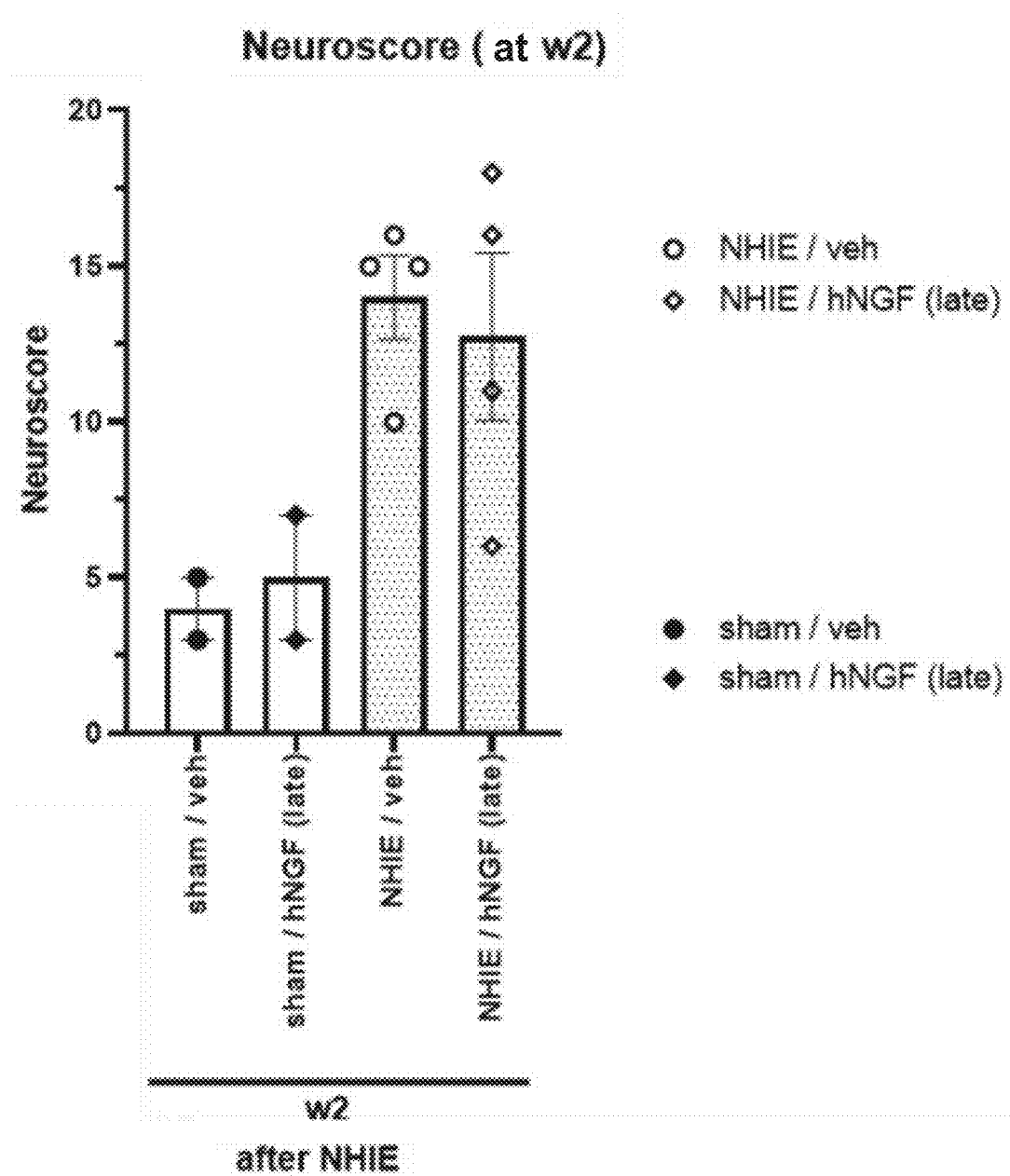
FIG. 10 shows the neuroscore of sham animal (treated with vehicle or with hNGF late) and NHIE animals (treated with vehicle or hNGF late) 2 weeks after induction of NHIE. The higher the score, the worse the outcome.

Neuroscore. The analysis of the sensorimotor deficits was carried out at week 2 after NHIE. The NHIE model caused overt sensorimotor deficits. The administration of hNGF (early) improved rats' behaviour at week 2 after NHIE as compared to vehicle (FIG. 9). A tendency in amelioration of sensorimotor deficits is apparent for NHIE rats receiving hNGF (late) (FIG. 10). Thus, both treatments showed a beneficial effect on sensorimotor deficits when compared to NHIE rats.

Figure 11:
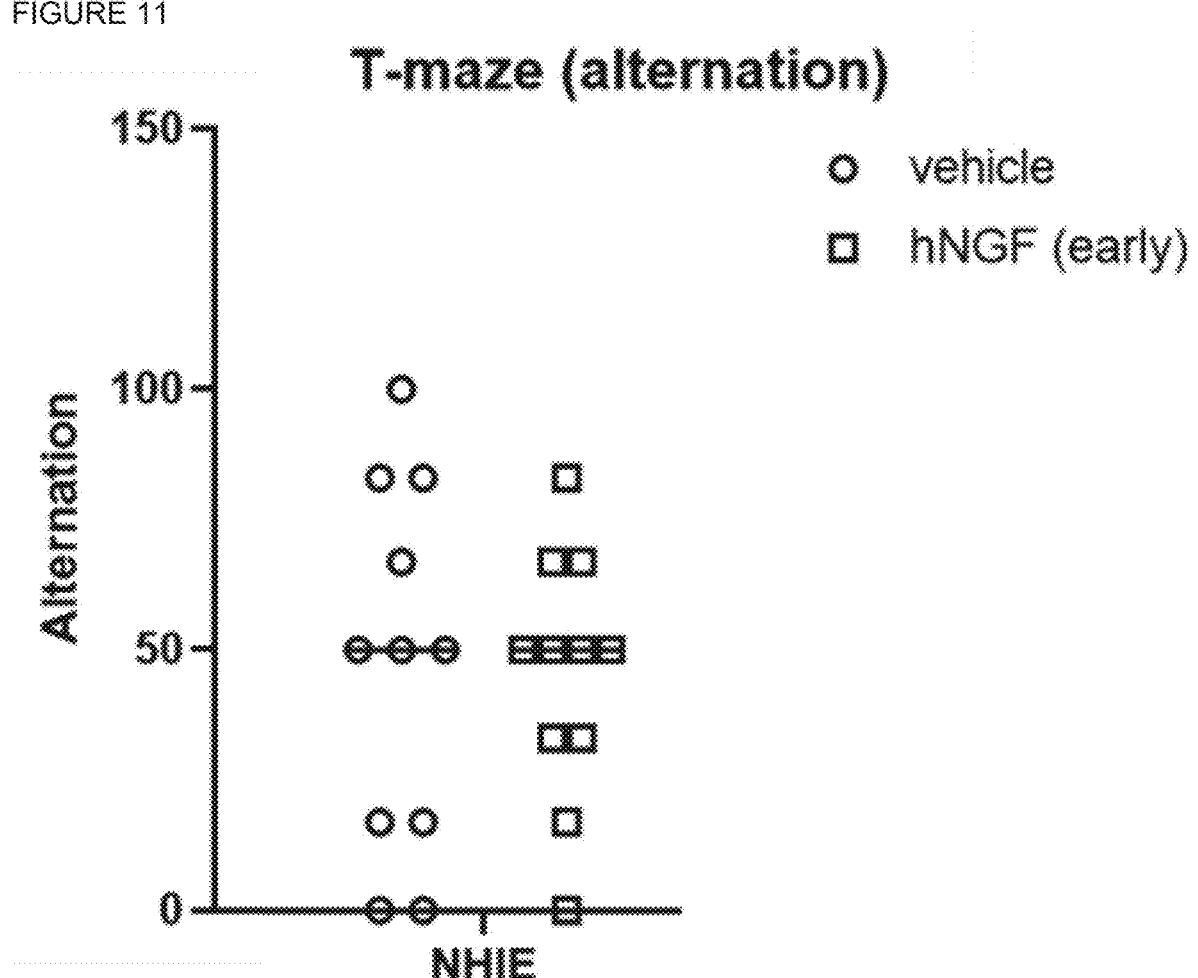
FIG. 11 shows alternation data assessed after NHIE induction (vehicle vs hNGF early-treated rats). The data are presented as median and individual values.
Figure 12:
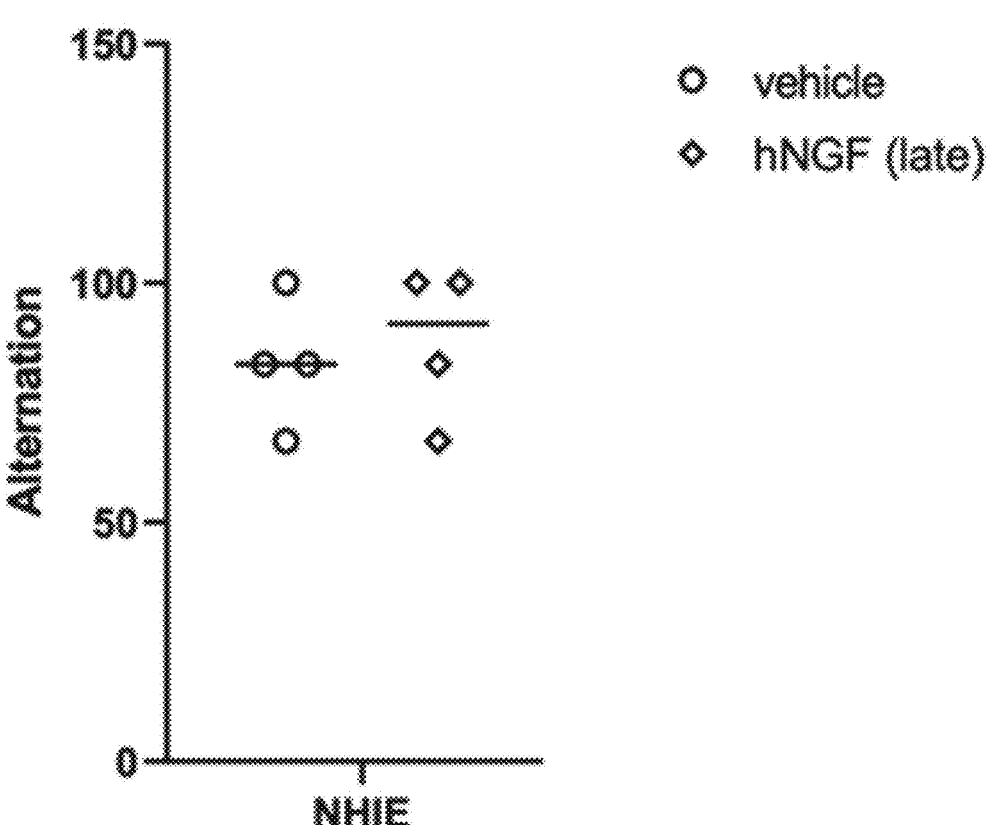
FIG. 12 shows alternation data assessed after NHIE induction (vehicle vs hNGF late-treated rats). The data are presented as median and individual values.

T-maze. The ability to alternate between two arms of a T-maze was assessed at week 3 after induction of NHIE. NHIE induced a small deficit in the ability to alternate the maze arms by the rats. No effect was observed after hNGF (early) (FIG. 11). Conversely, the data relative to the NHIE rats receiving hNGF (late) showed preserved alternation ability as compared to those receiving vehicle (FIG. 12).

Figure 13:
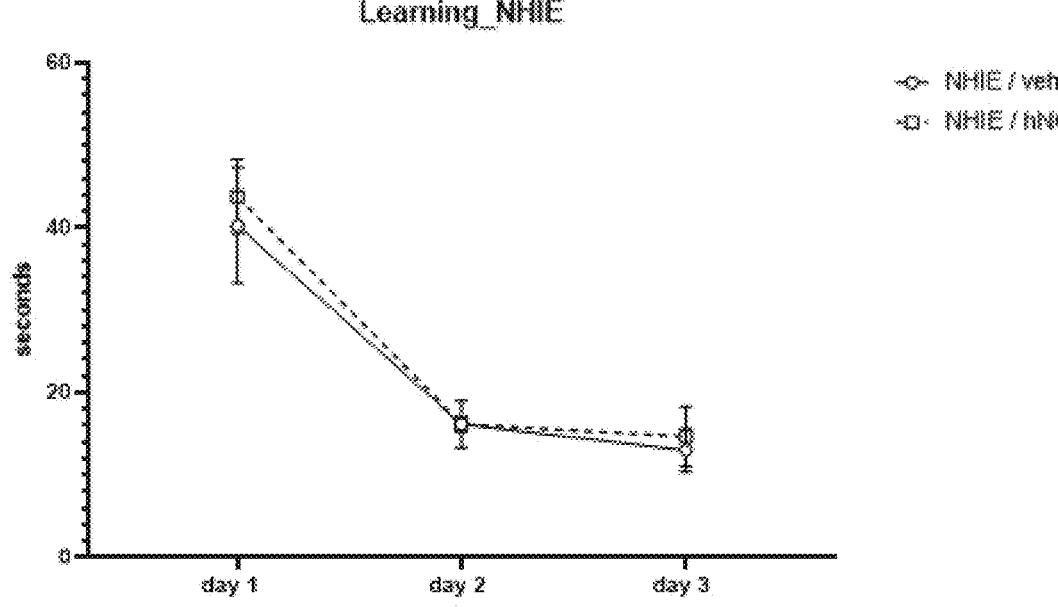
FIG. 13 shows primary latency (in seconds) to reach the escape hole in the maze for NHIE rats treated with vehicle or with hNGF (early). Data as mean±SEM.
Figure 14:
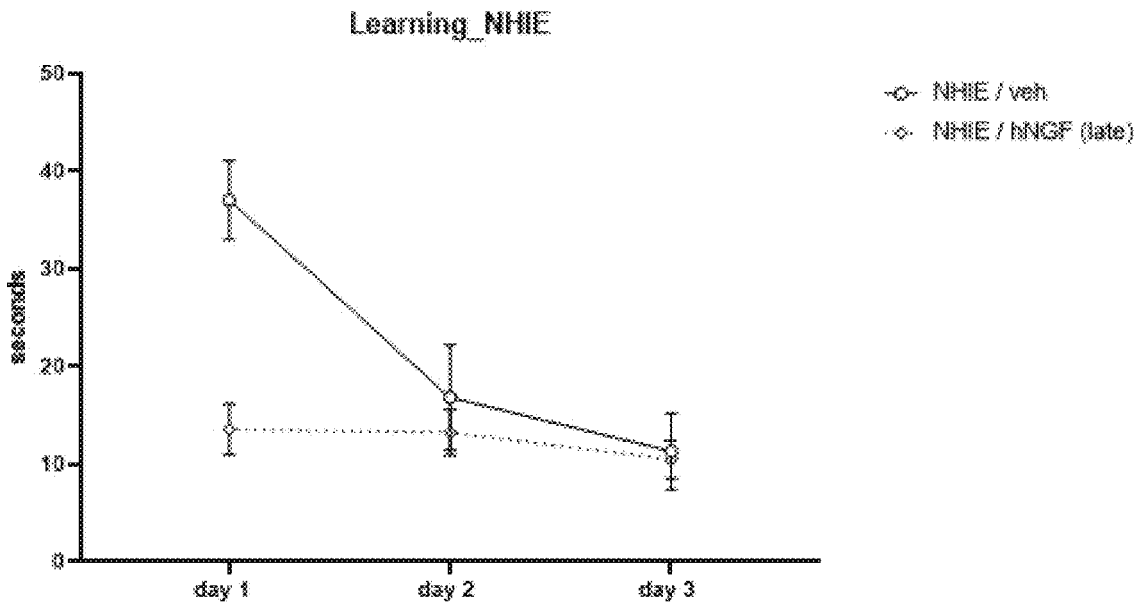
FIG. 14 shows primary latency (in seconds) to reach the escape hole in the maze for NHIE rats treated with vehicle or with hNGF (late). Data as mean±SEM.

Barnes maze. This test, which was carried out 28 days after induction of NHIE, evaluates learning and memory tasks. Over the three days of training, all rats could learn the position of the escape hole in the maze (FIG. 13 and FIG. 14). No effect was observed after hNGF (early) (FIG. 13). Of note, NHIE rats receiving hNGF (late) could quickly find the escape hole since day 1 (FIG. 14).

Figure 15:
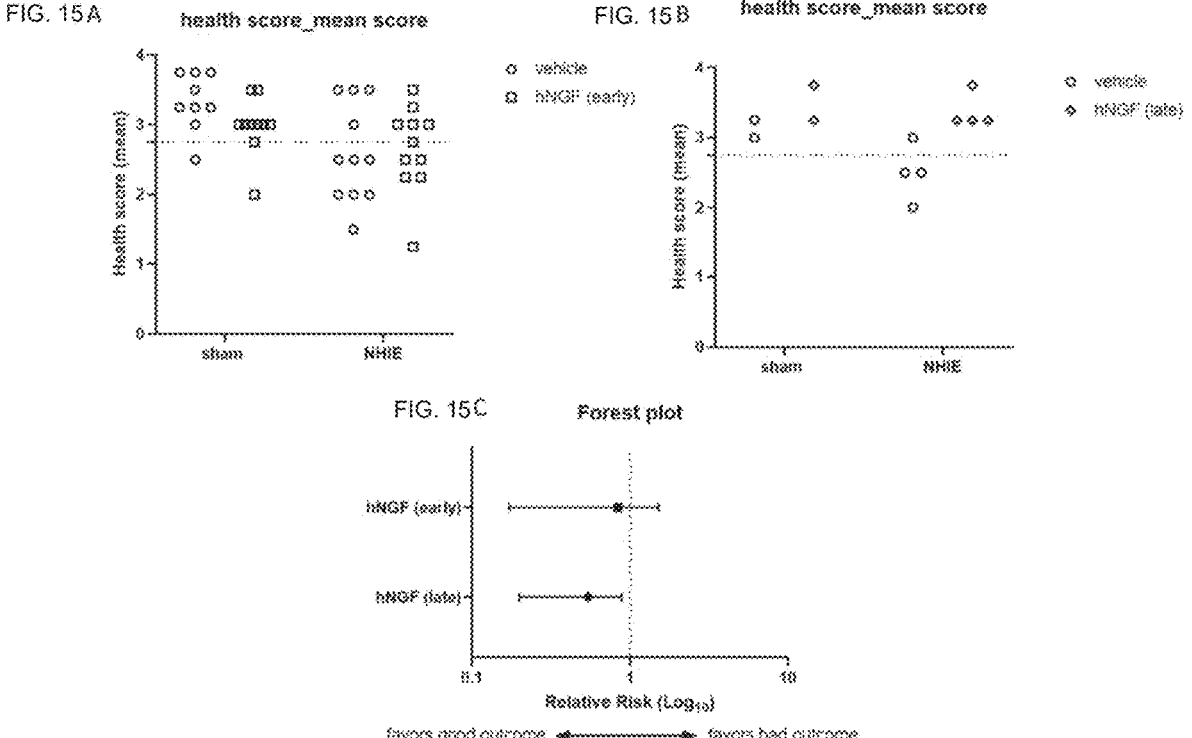
FIGS. 15A and 15B show individual comprehensive health scores for each rat, splitting the data for the early (FIG. 15A) or late (FIG. 15B) treatments.
FIG. 15C shows a forest plot of contingency analysis by the Chi-square test (*p<0.05).

Comprehensive health score. The data described above represent different aspects of rats' health, including weight growth, and the sensorimotor and cognitive deficits. A comprehensive score based on the distribution of each animal into quartiles of the different readouts (weight at P42, neuroscore at w2, T-maze at w3 and Barnes maze at w4) was created. The quartiles were defined in the NHIE/veh group. Data falling into the Q4 (best performance) obtained 4 points, the data falling in the other quartiles were scored accordingly to 1—worst score (FIG. 15A-15B). A cut-off of 2.75 indicating a good outcome was considered for contingency analysis (FIG. 15C). NHIE rats had a worse outcome than sham, and those receiving hNGF (late) showed the best score among NHIE rats. This is indicative of a surprisingly higher efficacy in restoring the health status of the late administration of hNGF compared to the early administration of hNGF in NHIE rats.

Figure 16:
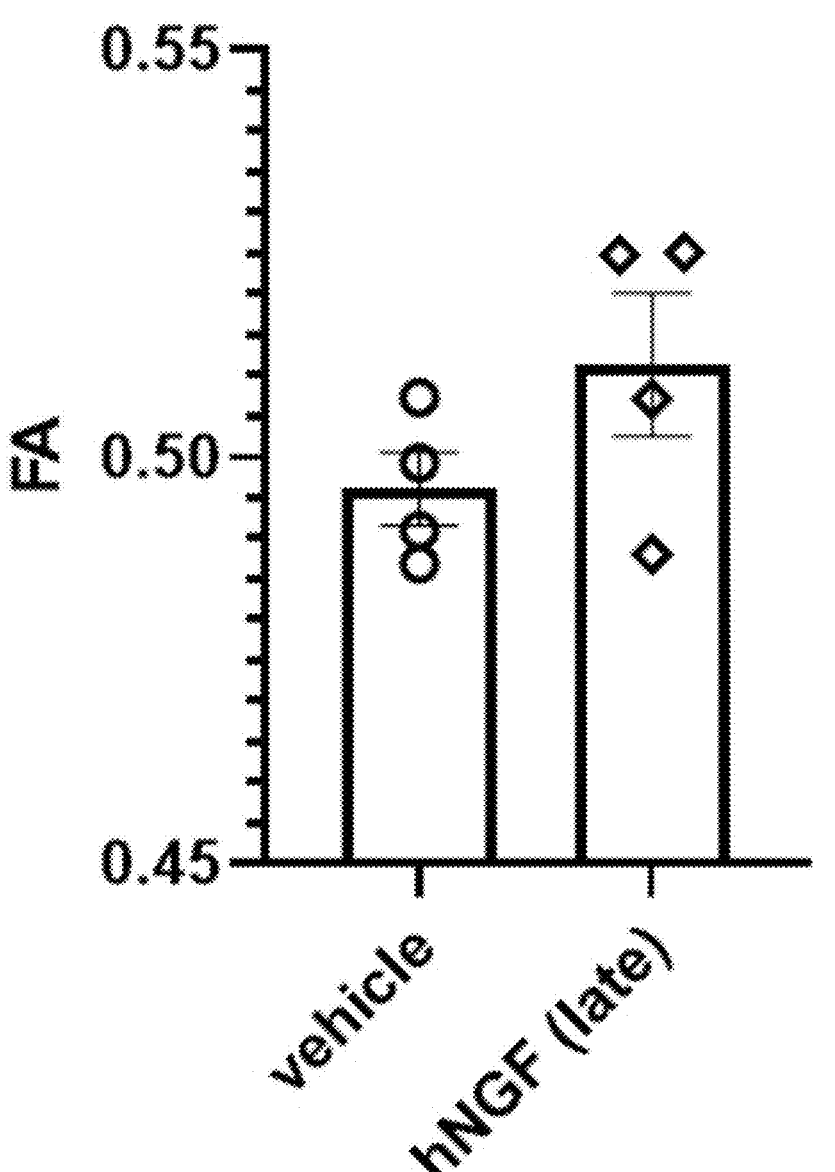
FIG. 16 shows fractional anisotropy (FA) value measured by diffusion tensor imaging (DTI), for rats treated with vehicle or with hNGF (late). A reduction of FA value is indicative of a damage to the white matter.

MRI. The effect on white matter damage was assessed at 5 weeks post-injury by diffusion tensor imaging (DTI) MRI analysis. As shown in FIG. 16, NHIE rats receiving hNGF (late) showed an increase in fractional anisotropy as compared to those receiving vehicle, suggesting a protective effect of hNGF on white matter.

Comprehensively, the results discussed above demonstrate that the administration of hNGF in a rat model of NHIE has beneficial effects both on sensorimotor and cognitive deficits typical of this disease. Surprisingly, the late administration of hNGF showed superior efficacy on cognitive deficits compared to the early administration of hNGF, which could be useful in identifying a window of treatment in humans to maximize the effects of hNGF on motor impairment and neurodevelopmental disabilities caused by NHIE.

Example 4

A study is performed to evaluate the efficacy, safety, pharmacokinetics, and immunogenicity of a pharmaceutical composition comprising nerve growth factor (NGF) for the treatment of neonatal hypoxic-ischemic encephalopathy (NHIE) in infants. The study population will include infants diagnosed with NHIE based on the Modified Sarnat Staging. Eligible participants may have undergone standard therapeutic hypothermia within six hours of birth.

The study will consist of a control group receiving standard care (therapeutic hypothermia only) and experimental groups receiving varying doses of a pharmaceutical composition that includes NGF, administered intranasally. The pharmaceutical composition including of recombinant human NGF (rhNGF) in a sterile solution or suspension, designed for safe and effective neonatal administration.

The inclusion criteria for the study require that the parent or legal guardian provide informed consent, demonstrating full comprehension of the informed consent form (ICF). This includes understanding the nature and purpose of the study, potential risks and side effects, and the ability to cooperate with the investigator while complying with all study requirements. Both male and female participants are eligible. The study includes infants born at a gestational age of more than 36 weeks and between the corrected ages of 1 to 3 months. Participants must have experienced perinatal depression, as indicated by at least one of the following: an Apgar score of less than 5 at 10 minutes, the need for resuscitation (such as chest compressions, mechanical ventilation, or CPAP) at 10 minutes of age, a cord blood gas or neonatal blood gas (obtained within 60 minutes of birth) with a pH lower than 7.00, or a base deficit of 15 mmol/L or greater in a cord or neonatal blood gas sample (arterial or venous) taken within the first 60 minutes after birth. Additionally, participants must have a diagnosis of neonatal hypoxic-ischemic encephalopathy (NHIE) classified as stage 2 or 3 according to the Modified Sarnat staging. Finally, all participants must have received standard therapeutic hypothermia treatment initiated within the first six hours after birth.

The exclusion criteria for the study include a birth weight of less than 1800 grams and microcephaly, defined as a head circumference three standard deviations or more below the mean for gestational age. Patients in extremis, those with motor impairment due to causes other than the study condition as determined by the investigators, and individuals with congenital malformations that pose an unacceptable risk to safety or interfere with study evaluations are also excluded. Additionally, participants with a positive newborn genetic screening for neurodevelopmental disorders (NDD) and/or neuromuscular disorders (NMD) identified through chromosomal microarray analysis, whole exome sequencing, or genome sequencing are not eligible. The study also excludes individuals taking certain concomitant medications (to be determined), those who have recently undergone surgical procedures or are scheduled for surgery during the study, and patients who have participated in, are currently participating in, or plan to participate in another interventional study within a defined period. Lastly, individuals unable to comply with study procedures will be excluded.

Tau, neurofilament light (NfL), and glial fibrillary acidic protein (GFAP). Additionally, the study will evaluate the neuroendocrine profile by measuring levels of vasopressin (ADH), cortisol, adrenocorticotropic hormone (ACTH), thyroid-stimulating hormone (TSH), T3, and T4.

Assessment criteria for normal, mild, moderate, and severe forms of NHIE are shown in Table 1.

TABLE 1

| Assessment Criteria | Normal (N) | Mild | Moderate (Mod) | Severe (S) |
|---|---|---|---|---|
| Level of Consciousness | Alert/arouses appropriately | Hyperalert | Lethargic | Stupor or coma |
| Spontaneous Activity | Normal | Normal or increased | Decreased | None |
| Posture | Normal | Normal or mild distal flexion | Distal flexion, complete extension | Decerebrate |
| Tone* | Normal | Normal or increased in trunk and extremities | Hypotonia (focal or general) | Flaccid |
| Suck Reflex | Normal | Normal or incomplete | Weak | Absent |
| Moro reflex | Strong | Strong, low threshold | Incomplete | Absent |
| Autonomic system | Pupils equal and reacting to light; normal heart rate and respirations | Pupils equal and reacting to light; normal heart rate and respirations | Pupils constricted; bradycardia or periodic/irregular breathing | Pupils deviated/dilated/non-reactive; variable heart rate or apnoea |
| Seizures | None | None | Common, focal or multifocal | Uncommon (excluding decrebration) |

*Assess tone in both limbs and trunk/neck - presence of hypotonia in either meets the criteria.

The primary objective of the study is to evaluate the efficacy of intranasal cenegermin in infants diagnosed with neonatal hypoxic-ischemic encephalopathy (NHIE) at birth in reducing the incidence of major neurodevelopmental disabilities by two years of age. Secondary objectives include assessing its efficacy in reducing the incidence of cerebral palsy and other neurodevelopmental disabilities, as well as evaluating its safety and tolerability throughout the study treatment. Additionally, the study aims to determine the systemic pharmacokinetic characteristics of intranasal cenegermin following administration and to assess its immunogenicity in infants diagnosed with NHIE. As an exploratory objective, the study will also assess biomarkers related to target engagement.

The primary endpoint of the study is the assessment of neurodevelopmental outcomes using the Bayley Scales of Infant and Toddler Development-4, evaluating cognitive, language, motor, social-emotional, and adaptive behavior domains. Secondary endpoints include standardized neurological examinations classified under the Gross Motor Function Classification System (GMFCS), brain MRI findings, and assessments using EEG, visual evoked potentials (VEPs), motor evoked potentials (MEPs), and brainstem auditory evoked potentials (BAEPs). Additional secondary outcomes involve autism assessments, quality of life (QoL) questionnaires, and monitoring the incidence of treatment-emergent serious and non-serious adverse events throughout the study. The study will also measure changes in serum levels of anti-drug antibodies (ADA) from baseline through 30 days after initiating intranasal cenegermin treatment. Exploratory endpoints will focus on neuroinflammatory biomarkers, including IL-1B, IL-6, IL-8, TNF-α, IL-10, IFN-γ, and MIP-1α, as well as neural injury markers such as

EMBODIMENTS

Embodiment 1 (E1). Nerve growth factor (NGF) for use in the prevention and/or treatment of neurodevelopmental disability associated with (e.g. affected or caused by) neonatal hypoxic-ischemic encephalopathy in a subject, wherein the NGF is administered intranasally to the subject.

E2. NGF for use as in E1, wherein the NGF is for use in curing neurodevelopmental disability associated with (e.g. affected or caused by) neonatal hypoxic-ischemic encephalopathy in the subject.

E3. NGF for use according to E1 or E2, wherein the NGF is for use in slowing down neurodevelopmental disability associated with (e.g. affected or caused by) neonatal hypoxic-ischemic encephalopathy in the subject.

E4. NGF for use according to any one of E1 to E3, wherein the NGF is for use in lessening the severity of neurodevelopmental disability associated with (e.g. affected or caused by) neonatal hypoxic-ischemic encephalopathy in the subject.

E5. NGF for use according to any one of E1 to E4, wherein the NGF is for use in halting the progression of neurodevelopmental disability associated with (e.g. affected or caused by) neonatal hypoxic-ischemic encephalopathy in the subject.

E6. NGF for use according to any one of E1 to E5, wherein the NGF is for use in slowing the development of neurodevelopmental disability associated with (e.g. affected or caused by) neonatal hypoxic-ischemic encephalopathy in the subject.

E7. NGF for use according to any one of E1 to E6, wherein the NGF is for use in improving neurodevelopmental disability associated with (e.g. affected or caused by) neonatal hypoxic-ischemic encephalopathy in the subject to a level compatible with the execution of daily activities typical of a subject of the same age which is not affected by neonatal hypoxic-ischemic encephalopathy.

E8. NGF for use according to E7, wherein the daily activities include basic movements such as crawling, walking, or controlling voluntary muscle actions, sitting straight, eating, grasping objects and interacting with the surrounding environment.

E9. NGF for use according to any one of E1 to E8, wherein the neurodevelopmental disability is motor impairment or one or more symptoms thereof.

E10. NGF for use according to E9, wherein the one or more symptoms thereof are selected from the group consisting of difficulties in movement, difficulties in muscle coordination, difficulties in motor skills, weakness, poor muscle tone and motor delays.

E11. NGF for use according to E9 or E10, wherein the motor impairment is caused by a muscle tone deregulation.

E12. NGF for use according to any one of E9 to E11, wherein the NGF is for use in normalizing the muscle tone of the subject.

E13. NGF for use according to E12, wherein normalizing the muscle tone of the subject includes returning the muscle tone of the subject to a level substantially comparable to the muscle tone of a subject of the same age without neonatal hypoxic-ischemic encephalopathy.

E14. NGF for use according to any one of E9 to E13, wherein the motor impairment or the muscle tone deregulation is associated with (e.g. affected or caused by) cerebral palsy.

E15. NGF for use according to any one of E11 to E14, wherein the muscle tone deregulation is selected from the group consisting of hypotonia, flaccidity, hypertonia, dystonia, ataxia, extrapyramidal symptoms, diplegia, tetraplegia, quadriplegia, hemiplegia and paraplegia.

E16. NGF for use according to E15, wherein the hypotonia is selected from focal hypotonia and general hypotonia.

E17. NGF for use according to E15 or E16, wherein the dystonia is selected from focal dystonia, segmental dystonia and general dystonia.

E18. NGF for use according to any one of E15 to E17, wherein the hypertonia is selected from spasticity, rigidity and paratonia.

E19. NGF for use according to any one of E9 to E18, wherein the subject has been diagnosed with a motor impairment associated with (e.g. affected or caused by) neonatal hypoxic ischemic encephalopathy (HIE) and the NGF is for use in the treatment of motor impairment in the subject, by intranasal administration to the subject.

E20. NGF for use according to any one of E9 to E18, wherein the subject has been identified as being at risk of developing a motor impairment associated with (e.g. affected or caused by) neonatal hypoxic ischemic encephalopathy (HIE) and the NGF is for use in the prevention of motor impairment in the subject prior to the development of the motor impairment, by intranasal administration to the subject.

E21. NGF for use according to any one of E1 to E8, wherein the neurodevelopmental disability is cerebral palsy or a clinical manifestation thereof.

E22. NGF for use according to E21, wherein the clinical manifestation is selected from motor impairment or one or more symptoms thereof and cognitive impairment.

E23. NGF for use according to E22, wherein the one or more symptoms of motor impairment are selected from the group consisting of difficulties in movement, difficulties in muscle coordination, difficulties in motor skills, weakness, poor muscle tone and motor delays.

E24. NGF for use according to E22 or E23, wherein the motor impairment is caused by a muscle tone deregulation.

E25. NGF for use according to any one of E22 to E24, wherein the NGF is for use in normalizing the muscle tone of the subject.

E26. NGF for use according to E25, wherein normalizing the muscle tone of the subject includes returning the muscle tone of the subject to a level substantially comparable to the muscle tone of a subject of the same age without neonatal hypoxic-ischemic encephalopathy.

E27. NGF for use according to any one of E24 to E26, wherein the muscle tone deregulation is selected from the group consisting of hypotonia, flaccidity, hypertonia, dystonia, ataxia, extrapyramidal symptoms, diplegia, tetraplegia, quadriplegia, hemiplegia and paraplegia.

E28. NGF for use according to E27, wherein the hypotonia is selected from focal hypotonia and general hypotonia.

E29. NGF for use according to E27 or E28, wherein the dystonia is selected from focal dystonia, segmental dystonia and general dystonia.

E30. NGF for use according to any one of E27 to E29, wherein the hypertonia is selected from spasticity, rigidity and paratonia.

E31. NGF for use according to any one of E21 to E30, wherein the subject has been diagnosed with cerebral palsy associated with (e.g. affected or caused by) neonatal hypoxic-ischemic encephalopathy and said NGF is for use in the treatment of said cerebral palsy in said subject, by intranasal administration to the subject.

E32. NGF for use according to any one of E21 to E30, wherein the subject has been identified as being at risk of developing cerebral palsy associated with (e.g. affected or caused by) neonatal hypoxic-ischemic encephalopathy and said NGF is for use in the prevention of said cerebral palsy in said subject, by intranasal administration to said subject.

E33. NGF for use according to any one of E1 to E8, wherein the neurodevelopmental disability is cognitive impairment.

E34. NGF for use according to any one of E1 to E8, wherein the neurodevelopmental disability is behavioral impairment.

E35. NGF for use according to any one of E1 to E8, wherein the neurodevelopmental disability is sensory impairment.

E36. NGF for use in promoting neurodevelopment in a subject diagnosed with neonatal hypoxic-ischemic encephalopathy, wherein the NGF is administered intranasally to the subject.

E37. NGF for use according to E36, wherein promoting neurodevelopment includes enhancing neuronal survival, synaptic formation, and/or the establishment of neural networks necessary for proper cognitive, motor, and sensory function.

E38. NGF for use according to any one of E1 to E37, wherein the neonatal hypoxic-ischemic encephalopathy (HIE) is selected from mild neonatal hypoxic-ischemic encephalopathy (HIE) (stage 1), moderate neonatal hypoxic-ischemic encephalopathy (HIE) (stage 2) and severe neonatal hypoxic-ischemic encephalopathy (HIE) (stage 3) as determined according to the staging system developed by Sarnat and Sarnat (Sarnat H B, Sarnat M S. Arch Neurol 1976; 33:696-705).

E39. NGF for use according to any one of E1 to E38, wherein the subject has a gestational age at birth of at least 36 weeks.

E40. NGF for use according to any one of E1 to E39, wherein the subject weighs at least 1800 grams at birth.

E41. NGF for use according to any one of E1 to E40, wherein the subject has at least one of the following signs of perinatal depression:

Apgar score less than 5 at 10 minutes of age, need for resuscitation (e.g., chest compressions, mechanical ventilation, or CPAP) at 10 minutes of age, pH less than 7.00 in a cord blood gas, or in a neonate blood gas obtained at a time less than 60 minutes of age, base deficit ≥15 mmol/L, or ≥12 mmol/L, or ≥16 mmol/L in a cord (arterial or venous) gas, or in an infant gas (arterial or venous) obtained at a time less than 60 minutes of age.

E42. NGF for use according to any one of E1 to E41, wherein the subject has been treated with therapeutic hypothermia started prior to 6 hours after birth.

E43. NGF for use according to any one of E1 to E42, wherein NGF is administered to the subject for the first time within one month after birth (e.g., 1 day to 30 days), preferably within seven days after birth, more preferably within 72 hours after birth, more preferably within 36 hours after birth, and even more preferably within 24 hours after birth.

E44. NGF for use according to any one of E1 to E42, wherein NGF is administered to the subject for the first time one month or later after birth, preferably between one month and 36 months after birth, more preferably between one month and four months after birth.

E45. NGF for use according to any one of E1 to E42, wherein NGF is administered to the subject for the first time between three and nine months after birth, preferably between three and six months after birth.

E46. NGF for use according to any one of E1 to E45, wherein NGF is administered to the subject with an intermittent administration schedule, with two or more cycles of periods of treatment alternated by wash-out periods.

E47. NGF for use according to E46, wherein NGF is administered to the subject for at least three cycles, wherein each cycle comprises seven days of daily intranasal administration of NGF followed by 21 days of washout.

E48. NGF for use according to any one of E1 to E47, wherein the total dose of NGF that is administered to the subject is between 25 μg/kg and 400 μg/kg, preferably between 30 μg/kg and 300 μg/kg, more preferably between 35 μg/kg and 200 μg/kg, more preferably between 40 μg/kg and 100 μg/kg, more preferably between 40 μg/kg and 60 μg/kg, more preferably between 45 μg/kg and 55 μg/kg, even more preferably it is 50 μg/kg.

E49. NGF for use according to any one of E46 to E49, wherein the dose per cycle of NGF that is administered to the subject is between 15 μg/kg and 20 μg/kg, most preferably 16.7 μg/kg.

E50. NGF for use according to any one of E1 to E49, wherein the daily dose of NGF that is administered to the subject is between 2 μg/kg and 3 μg/kg, more preferably 2.4 μg/kg.

E51. NGF for use according to any one of E1 to E50, wherein the dose per nostril of NGF that is administered to the subject is between 0.3 μg/kg/nostril and 1 μg/kg/nostril, most preferably 0.6 μg/kg/nostril.

E52. NGF for use according to any one of E1 to E51, wherein the daily dose of NGF is administered to the subject twice daily with a 12-hour interval.

E53. NGF for use according to any one of E1 to E52, wherein the NGF is human NGF.

E54. NGF for use according to any one of E1 to E53, wherein the human NGF has the amino acid sequence of SEQ ID NO:1.

E55. NGF for use according to any one of E1 to E53, wherein the human NGF has the amino acid sequence of SEQ ID NO:2.

E56. NGF for use according to any one of E1 to E53, wherein the human NGF is a mixture of NGFs having sequences of SEQ ID NO:1 and SEQ ID NO:2.

E57. NGF for use according to any one of E1 to E56, wherein NGF is produced by recombinant DNA technology.

E58. NGF for use according to any one of E1 to E57, wherein NGF is a human recombinant NGF (rhNGF).

E59. NGF for use according to E58, wherein NGF is a human recombinant NGF (rhNGF) produced by a method as described in WO0022119 A1 or WO2013092776 A1.

E60. NGF for use according to any one of E1 to E59, wherein NGF has a purity higher than 70%.

E61. NGF for use according to any one of E1 to E60, wherein NGF has a purity higher than 80%, higher than 90%, higher than 95%, higher than 98%, or higher than 99%.

E62. NGF for use according to E60 or E61, wherein the purity of NGF is determined by HPLC.

E63. A pharmaceutical composition for intranasal administration comprising NGF as described in any one of E1 to E62 and at least one pharmaceutically acceptable excipient, for use in the prevention and/or treatment of neurodevelopmental disability associated with (e.g. affected or caused by) neonatal hypoxic-ischemic encephalopathy in a subject, wherein the pharmaceutical composition is administered intranasally to the subject.

E64. Pharmaceutical composition for use as in E63, wherein the pharmaceutical composition is for use in curing neurodevelopmental disability associated with (e.g. affected or caused by) neonatal hypoxic-ischemic encephalopathy in the subject.

E65. Pharmaceutical composition for use according to E63 or E64, wherein the pharmaceutical composition is for use in slowing down neurodevelopmental disability associated with (e.g. affected or caused by) neonatal hypoxic-ischemic encephalopathy in the subject.

E66. Pharmaceutical composition for use according to any one of E63 to E65, wherein the pharmaceutical composition is for use in lessening the severity of neurodevelopmental disability associated with (e.g. affected or caused by) neonatal hypoxic-ischemic encephalopathy in the subject.

E67. Pharmaceutical composition for use according to any one of E63 to E66, wherein the pharmaceutical composition is for use in halting the progression of neurodevelopmental disability associated with (e.g. affected or caused by) neonatal hypoxic-ischemic encephalopathy in the subject.

E68. Pharmaceutical composition for use according to any one of E63 to E67, wherein the pharmaceutical composition is for use in slowing the development of neurodevelopmental disability associated with (e.g. affected or caused by) neonatal hypoxic-ischemic encephalopathy in the subject.

E69. Pharmaceutical composition for use according to any one of E63 to E68, wherein the pharmaceutical composition is for use in improving neurodevelopmental disability associated with (e.g. affected or caused by) neonatal hypoxic-ischemic encephalopathy in the subject to a level compatible with the execution of daily activities typical of a subject of the same age which is not affected by neonatal hypoxic-ischemic encephalopathy.

E70. Pharmaceutical composition for use according to E69, wherein the daily activities include basic movements such as crawling, walking, or controlling voluntary muscle actions, sitting straight, eating, grasping objects and interacting with the surrounding environment.

E71. Pharmaceutical composition for use according to any one of E63 to E70, wherein the neurodevelopmental disability is motor impairment or one or more symptoms thereof.

E72. Pharmaceutical composition for use according to E71, wherein the one or more symptoms thereof are selected from the group consisting of difficulties in movement, difficulties in muscle coordination, difficulties in motor skills, weakness, poor muscle tone and motor delays.

E73. Pharmaceutical composition for use according to E71 or E72, wherein the motor impairment is caused by a muscle tone deregulation.

E74. Pharmaceutical composition for use according to any one of E71 to E73, wherein the pharmaceutical composition is for use in normalizing the muscle tone of the subject.

E75. Pharmaceutical composition for use according to E74, wherein normalizing the muscle tone of the subject includes returning the muscle tone of the subject to a level substantially comparable to the muscle tone of a subject of the same age without neonatal hypoxic-ischemic encephalopathy.

E76. Pharmaceutical composition for use according to any one of E71 to E75, wherein the motor impairment or the muscle tone deregulation is associated with (e.g. affected or caused by) cerebral palsy.

E77. Pharmaceutical composition for use according to any one of E73 to E76, wherein the muscle tone deregulation is selected from the group consisting of hypotonia, flaccidity, hypertonia, dystonia, ataxia, extrapyramidal symptoms, diplegia, tetraplegia, quadriplegia, hemiplegia and paraplegia.

E78. Pharmaceutical composition for use according to E77, wherein the hypotonia is selected from focal hypotonia and general hypotonia.

E79. Pharmaceutical composition for use according to E77 or E78, wherein the dystonia is selected from focal dystonia, segmental dystonia and general dystonia.

E80. Pharmaceutical composition for use according to any one of E77 to E79, wherein the hypertonia is selected from spasticity, rigidity and paratonia.

E81. Pharmaceutical composition for use according to any one of E71 to E80, wherein the subject has been diagnosed with a motor impairment associated with (e.g. affected or caused by) neonatal hypoxic ischemic encephalopathy (HIE) and the pharmaceutical composition is for use in the treatment of motor impairment in the subject, by intranasal administration to the subject.

E82. Pharmaceutical composition for use according to any one of E71 to E80, wherein the subject has been identified as being at risk of developing a motor impairment associated with (e.g. affected or caused by) neonatal hypoxic ischemic encephalopathy (HIE) and the pharmaceutical composition is for use in the prevention of motor impairment in the subject prior to the development of the motor impairment, by intranasal administration to the subject.

E83. Pharmaceutical composition for use according to any one of E63 to E70, wherein the neurodevelopmental disability is cerebral palsy or a clinical manifestation thereof.

E84. Pharmaceutical composition for use according to E83, wherein the clinical manifestation is selected from motor impairment or one or more symptoms thereof and cognitive impairment.

E85. Pharmaceutical composition for use according to E84, wherein the one or more symptoms of motor impairment are selected from the group consisting of difficulties in movement, difficulties in muscle coordination, difficulties in motor skills, weakness, poor muscle tone and motor delays.

E86. Pharmaceutical composition for use according to E84 or E85, wherein the motor impairment is caused by a muscle tone deregulation.

E87. Pharmaceutical composition for use according to any one of E84 to E86, wherein the pharmaceutical composition is for use in normalizing the muscle tone of the subject.

E88. Pharmaceutical composition for use according to E87, wherein normalizing the muscle tone of the subject includes returning the muscle tone of the subject to a level substantially comparable to the muscle tone of a subject of the same age without neonatal hypoxic-ischemic encephalopathy.

E89. Pharmaceutical composition for use according to any one of E85 to E88, wherein the muscle tone deregulation is selected from the group consisting of hypotonia, flaccidity, hypertonia, dystonia, ataxia, extrapyramidal symptoms, diplegia, tetraplegia, quadriplegia, hemiplegia and paraplegia.

E90. Pharmaceutical composition for use according to E89, wherein the hypotonia is selected from focal hypotonia and general hypotonia.

E91. Pharmaceutical composition for use according to E89 or E90, wherein the dystonia is selected from focal dystonia, segmental dystonia and general dystonia.

E92. Pharmaceutical composition for use according to any one of E89 to E91, wherein the hypertonia is selected from spasticity, rigidity and paratonia.

E93. Pharmaceutical composition for use according to any one of E83 to E92, wherein the subject has been diagnosed with cerebral palsy associated with (e.g.

affected or caused by) neonatal hypoxic-ischemic encephalopathy and said pharmaceutical composition is for use in the treatment of said cerebral palsy in said subject, by intranasal administration to the subject.

E94. Pharmaceutical composition for use according to any one of E83 to E92, wherein the subject has been identified as being at risk of developing cerebral palsy associated with (e.g. affected or caused by) neonatal hypoxic-ischemic encephalopathy and said pharmaceutical composition is for use in the prevention of said cerebral palsy in said subject, by intranasal administration to said subject.

E95. Pharmaceutical composition for use according to any one of E63 to E70, wherein the neurodevelopmental disability is behavioral impairment or cognitive impairment.

E96. Pharmaceutical composition for use according to any one of E63 to E70, wherein the neurodevelopmental disability is sensory impairment.

E97. A pharmaceutical composition for intranasal administration comprising NGF as described in any one of E1 to E62 and at least one pharmaceutically acceptable excipient, for use in promoting neurodevelopment in a subject diagnosed with neonatal hypoxic-ischemic encephalopathy, wherein the pharmaceutical composition is administered intranasally to the subject.

E98. Pharmaceutical composition for use according to E97, wherein promoting neurodevelopment includes enhancing neuronal survival, synaptic formation, and/or the establishment of neural networks necessary for proper cognitive, motor, and sensory function.

E99. Pharmaceutical composition for use according to any one of E63 to E98, wherein the neonatal hypoxic-ischemic encephalopathy (HIE) is selected from mild neonatal hypoxic-ischemic encephalopathy (HIE) (stage 1), moderate neonatal hypoxic-ischemic encephalopathy (HIE) (stage 2) and severe neonatal hypoxic-ischemic encephalopathy (HIE) (stage 3) as determined according to the staging system developed by Sarnat and Sarnat (Sarnat H B, Sarnat M S. Arch Neurol 1976; 33:696-705).

E100. Pharmaceutical composition for use according to any one of E63 to E99, wherein the subject has a gestational age at birth of at least 36 weeks.

E101. Pharmaceutical composition for use according to any one of E63 to E100, wherein the subject weighs at least 1800 grams at birth.

E102. Pharmaceutical composition for use according to any one of E63 to E101, wherein the subject has at least one of the following signs of perinatal depression:
Apgar score less than 5 at 10 minutes of age,
need for resuscitation (e.g., chest compressions, mechanical ventilation, or CPAP) at 10 minutes of age,
pH less than 7.00 in a cord blood gas, or in a neonate blood gas obtained at a time less than 60 minutes of age,
base deficit ≥12 mmol/L, or ≥15 mmol/L, or ≥16 mmol/L in a cord (arterial or venous) gas, or in an infant gas (arterial or venous) obtained at a time less than 60 minutes of age.

E103. Pharmaceutical composition for use according to any one of E63 to E102, wherein the subject has been treated with therapeutic hypothermia started prior to 6 hours after birth.

E104. Pharmaceutical composition for use according to any one of E63 to E103, wherein the pharmaceutical composition is administered to the subject for the first time within one month after birth (e.g., 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days), preferably within seven days after birth, more preferably within 72 hours after birth (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours), more preferably within 36 hours after birth, and even more preferably within 24 hours after birth.

E105. Pharmaceutical composition for use according to any one of E63 to E103, wherein the pharmaceutical composition is administered to the subject for the first time starting one month or later after birth, preferably between one month and 36 months after birth, more preferably between one month and 24 months after birth, more preferably between one month and 12 months after birth, even more preferably between one month and six months after birth, and most preferably between one month and four months after birth.

E106. Pharmaceutical composition for use according to any one of E63 to E103, wherein the pharmaceutical composition is administered to the subject for the first time between three and nine months after birth, preferably between three and six months after birth.

E107. Pharmaceutical composition for use according to any one of E63 to E106, wherein the pharmaceutical composition is administered to the subject with an intermittent administration schedule, with two or more cycles of periods of treatment alternated by wash-out periods.

E108. Pharmaceutical composition for use according to E107, wherein the pharmaceutical composition is administered to the subject for at least three cycles, wherein each cycle comprises seven days of daily intranasal administration of NGF followed by 21 days of washout (i.e., a period wherein NGF is not administered to the subject).

E109. Pharmaceutical composition for use according to any one of E63 to E108, wherein the total dose of NGF that is administered to the subject is between 25 µg/kg and 400 µg/kg, preferably between 30 µg/kg and 300 µg/kg, more preferably between 35 µg/kg and 200 µg/kg, more preferably between 40 µg/kg and 100 µg/kg, more preferably between 40 µg/kg and 60 µg/kg, more preferably between 45 µg/kg and 55 µg/kg, even more preferably it is 50 µg/kg.

E110. Pharmaceutical composition for use according to any one of E107 to E109, wherein the dose per cycle of NGF that is administered to the subject is between 15 µg/kg and 20 µg/kg, more preferably between 16 µg/kg and 17 µg/kg, even more preferably between 16.6 µg/kg and 16.8 µg/kg, most preferably it is 16.7 µg/kg.

E111. Pharmaceutical composition for use according to any one of E63 to E110, wherein the daily dose of NGF that is administered to the subject is between 2 µg/kg and 3 µg/kg, preferably between 2.3 µg/kg and 2.5 µg/kg, more preferably it is 2.4 µg/kg.

E112. Pharmaceutical composition for use according to any one of E63 to E111, wherein the dose per nostril of NGF that is administered to the subject is between 0.3 µg/kg/nostril and 1 µg/kg/nostril, more preferably between 0.4 µg/kg/nostril and 0.8 µg/kg/nostril, more preferably between 0.5 µg/kg/nostril and 0.7 µg/kg/ nostril, most preferably it is 0.6 µg/kg/nostril.

E113. Pharmaceutical composition for use according to any one of E63 to E112, wherein the daily dose of NGF for use according to the present disclosure is administered to the subject twice daily with 12 hours interval.

E114. Pharmaceutical composition for use according to any one of E63 to E113, wherein the NGF is human NGF.

E115. Pharmaceutical composition for use according to any one of E63 to E114, wherein the human NGF has the amino acid sequence of SEQ ID NO:1 below

```
SEQ. ID NO: 1:
SSSHPIFHRGEFSVCDSVSVWVGDKTTATDIKGKEVMVLGEVNINNSVF
KQYFFETKCRDPNPVDSGCRGIDSKHWNSYCTTTHTFVKALTMDGKQAA
WRFIRIDTACVCVLSRKAVR.
```

E116. Pharmaceutical composition for use according to any one of E63 to E114, wherein the human NGF has the amino acid sequence of SEQ ID NO:2 below:

```
SEQ ID NO: 2:
SSSHPIFHRGEFSVCDSVSVWVGDKTTATDIKGKEVMVLGEVNINNSVF
KQYFFETKCRDPNPVDSGCRGIDSKHWNSYCTTTHTFVKALTMDGKQA
AWRFIRIDTACVCVLSRKAVRRA.
```

E117. Pharmaceutical composition for use according to any one of E63 to E114, wherein the human NGF is a mixture of NGFs having sequences of SEQ ID NO:1 and SEQ ID NO:2.

E118. Pharmaceutical composition for use according to any one of E63 to E117, wherein NGF is produced by recombinant DNA technology.

E119. Pharmaceutical composition for use according to any one of E63 to E118, wherein NGF is a human recombinant NGF (rhNGF).

E120. Pharmaceutical composition for use according to E119, wherein NGF is a human recombinant NGF (rhNGF) produced by a method as described in WO0022119 A1 or WO2013092776 A1.

E121. Pharmaceutical composition for use according to any one of E63 to E120, wherein NGF has a purity higher than 70%.

E122. Pharmaceutical composition for use according to any one of E63 to E121, wherein NGF has a purity higher than 80%, higher than 90%, higher than 95%, higher than 98%, or higher than 99%.

E123. Pharmaceutical composition for use according to E121 or E122, wherein the purity of NGF is determined by HPLC.

E124. Pharmaceutical composition for use according to any one of E63 to E123, wherein the pharmaceutical composition is a liquid intranasal composition.

E125. Pharmaceutical composition for use according to any one of E63 to E124, wherein the pharmaceutical composition comprises an effective amount of the NGF and at least one pharmaceutically acceptable excipient suitable for intranasal use.

E126. Pharmaceutical composition for use according to any one of E63 to E125, wherein the pharmaceutically acceptable excipient is selected from solvents, thickening agents, mucoadhesive agents, buffers, antioxidants, surfactants, preservatives, and penetration enhancers.

E127. Pharmaceutical composition for use according to any one of E124 to E126, wherein the concentration of the NGF in the liquid intranasal composition for use according to the disclosure is between about 5 µg/ml and about 1 mg/ml, preferably between about 10 g/ml and about 400 µg/ml, more preferably between about 15 µg/ml and about 200 µg/ml, even more preferably it is about 20 µg/ml.

E128. Pharmaceutical composition for use according to E126 or E127, wherein the solvent is water.

E129. Pharmaceutical composition for use according to any one of E126 to E128, wherein the mucoadhesive agent is glycerol.

E130. Pharmaceutical composition for use according to any one of E126 to E129, wherein the mucoadhesive agent (e.g., glycerol) is at a concentration between 0.05% w/v and 0.2% w/v, preferably at a concentration of 0.1% w/v.

E131. Pharmaceutical composition for use according to E126, wherein the antioxidant is methionine.

E132. Pharmaceutical composition for use according to E126 or E131, wherein the antioxidant (e.g., methionine) is at a concentration between about 0.005 mg/ml and about 0.02 mg/ml, preferably it is about 0.01 mg/ml.

E133. Pharmaceutical composition for use according to any one of E126 to E132, wherein the surfactant is Kolliphor P188.

E134. Pharmaceutical composition for use according to any one of E126 to E133, wherein the surfactant (e.g., Kolliphor P188) is at a concentration between about 0.05% w/v and about 0.2% w/v, preferably about 0.1% w/v.

E135. Pharmaceutical composition for use according to any one of E126 to E134, wherein the buffer is phosphate buffer.

E136. Pharmaceutical composition for use according to any one of E126 to E135, wherein the penetration enhancer is n-Dodecyl-β-D-maltoside.

E137. Pharmaceutical composition for use according to any one of E126 to E136, wherein the penetration enhancer (e.g., n-Dodecyl-β-D-maltoside) is at a concentration between about 0.1% w/v and about 1% w/v, preferably about 0.5% w/v.

E138. Pharmaceutical composition for use according to any one of E124 to E137, wherein the liquid intranasal composition comprises or consists of NGF, sodium chloride, phosphate buffer, and water.

E139. Pharmaceutical composition for use according to any one of E124 to E138, wherein the liquid intranasal composition comprises or consists of the NGF, sodium chloride, phosphate buffer, Kolliphor P188, L-Methionine, and water.

E140. Pharmaceutical composition for use according to any one of E124 to E139, wherein the liquid intranasal composition for use according to the disclosure comprises or consists of NGF, sodium chloride, phosphate buffer, Kolliphor P188, L-Methionine, Glycerol, n-Dodecyl-β-D-maltoside and water.

E141. Pharmaceutical composition for use according to any one of E124 to E140, wherein the liquid intranasal composition for use according to the disclosure comprises or consists of NGF, NaH2 PO4*H2O, NaCl, Kolliphor P188, -L-Methionine.

E142. Pharmaceutical composition for use according to any one of E124 to E141, wherein the liquid intranasal composition for use according to the disclosure comprises or consists of the following components:

NGF as described above, at a concentration:
between about 5 µg/ml and about 1 mg/ml,
between about 10 µg/ml and about 400 µg/ml, or
between about 15 µg/ml and about 200 µg/ml, NaH2 PO4*H2O, at a concentration:
between about 5 and about 8 mg/ml, or
at about 6.9 mg/mL, NaCl, at a concentration:
between about 5 and about 6.5 mg/ml, or
about 5.84 mg/mL, Kolliphor P188, at a concentration:
between about 0.05% w/v and about 0.2% w/v, or
about 0.1% w/v, L-Methionine, at a concentration:
between about 0.05 mg/ml and about 0.2 mg/ml, or
about 0.1 mg/ml, Optionally, n-Dodecyl-β-D-maltoside, at a concentration:
between about 0.1% w/v and about 1% w/v, or
about 0.5% w/v,
and/or glycerol, at a concentration:
between about 0.05% w/v and about 0.2% w/v, or
about 0.1% w/v, and Water.

E143. NGF for use according to any one of E1 to E62 or a pharmaceutical composition for use according to any one of E63 to E142, wherein the subject is a human subject.

E144. NGF or a pharmaceutical composition for use according to E143, wherein the subject is a neonate or an infant.

E145. Nerve growth factor (NGF) for use in the prevention and/or treatment of motor impairment associated with neonatal hypoxic-ischemic encephalopathy in a subject, wherein said NGF is administered intranasally to said subject.

E146. NGF for use according to E145, wherein said motor impairment is caused by a muscle tone deregulation.

E147. NGF for use according to E145 or E146, wherein said NGF is for use in normalizing the muscle tone of a subject with neonatal hypoxic-ischemic encephalopathy.

E148. NGF for use according to any one of E145 to E147, wherein said motor impairment or said muscle tone deregulation is associated with cerebral palsy.

E149. NGF for use according to any one of E145 to E148, wherein said muscle tone deregulation is selected from the group consisting of hypotonia, flaccidity, hypertonia, dystonia, ataxia, extrapyramidal symptoms, diplegia, tetraplegia, quadriplegia, hemiplegia and paraplegia.

E150. NGF for use according to E149, wherein said hypotonia is selected from focal hypotonia and general hypotonia.

E151. NGF for use according to E149, wherein said dystonia is selected from focal dystonia, segmental dystonia and general dystonia.

E152. NGF for use according to E149, wherein said hypertonia is selected from spasticity, rigidity and paratonia.

E153. NGF for use according to any one of E145 to E152, wherein said NGF is administered from one to three times a day for a period of treatment of between 7 and 90 days, preferably between 15 and 60 days.

E154. NGF for use according to any one of E145 to E153, wherein the amount of NGF per each administration is between 5 µg and 1 mg, more preferably between 10 µg and 400 µg, even more preferably between 15 µg and 200 µg, even more preferably 20 µg.

E155. A pharmaceutical composition for intranasal administration comprising NGF and at least one pharmaceutically acceptable excipient, for use in the prevention and/or treatment of motor impairment associated with neonatal hypoxic-ischemic encephalopathy (HIE) in a subject, wherein said pharmaceutical composition is administered intranasally to the subject.

E156. A pharmaceutical composition for use according to E155, wherein said NGF is present in the composition at a concentration between 5 µg/ml and 1 mg/ml, more preferably between 10 µg/ml and 400 µg/ml, even more preferably between 15 µg/ml and 200 µg/ml.

E157. A pharmaceutical composition for use according to E155 or E156, comprising, preferably consisting of NGF, sodium chloride, phosphate buffer and water.

E158. A pharmaceutical composition for use according to any one of E155 to E157, wherein said NGF is human NGF, more preferably it is recombinant human NGF.

E159. A pharmaceutical composition for use according to any one of E155 to E158, wherein said human NGF has the amino acid sequence of SEQ ID NO:1 or SEQ ID NO:2.

E160. NGF for use according to E1, E7-E18, E20-E30, E32-E62, wherein the NGF is for use in the reduction of the likelihood and/or reduction of severity of occurrence of said neurodevelopmental disability in said subject, by intranasal administration to said subject.

E161. NGF for use according to E145-E159, wherein the NGF is for use in the reduction of the likelihood and/or reduction of severity of occurrence of said motor impairment in said subject, by intranasal administration to said subject.

E162. A pharmaceutical composition for use according to any one of E63, E70-80, E82-92, E92-96, E99-144, wherein the pharmaceutical composition is for use in the reduction of the likelihood and/or reduction of severity of occurrence of said neurodevelopmental disability in said subject, by intranasal administration to said subject.

E163. NGF for use according to any one of E1 to E45, E48 to E62, E143 to E144, wherein NGF is administered to the subject with continuous administration schedule.

E164. Pharmaceutical composition for use according to any one of E63 to E106, E109 to E144, wherein the pharmaceutical composition is administered to the subject with continuous administration schedule.

E165. NGF or pharmaceutical composition for use according to any one of E1 to E164, wherein said NGF or pharmaceutical composition is administered intranasally to the subject.

What is claimed is:

1. A method of treating cerebral palsy associated with neonatal hypoxic-ischemic encephalopathy in a human subject in need thereof, the method comprising administering a therapeutically effective amount of nerve growth factor (NGF) intranasally to the subject only subsequent to a neonatal hypoxic-ischemic event, wherein the NGF comprises SEQ ID NO: 1.

2. The method of claim 1, wherein the subject has motor impairment that is caused by a muscle tone deregulation.

3. The method of claim 2, wherein the muscle tone deregulation is selected from the group consisting of hypotonia, flaccidity, hypertonia, dystonia, ataxia, extrapyramidal symptoms, diplegia, tetraplegia, quadriplegia, hemiplegia and paraplegia.

4. The method of claim 3, wherein the hypotonia is selected from focal hypotonia and general hypotonia.

5. The method of claim 3, wherein the dystonia is selected from focal dystonia, segmental dystonia and general dystonia.

6. The method of claim 3, wherein the hypertonia is selected from spasticity, rigidity, and paratonia.

7. The method of claim 1, wherein the administering normalizes muscle tone of the subject with neonatal hypoxic-ischemic encephalopathy to a level of muscle tone substantially comparable to a healthy subject of the same age.

8. The method of claim 1, wherein the subject has experienced perinatal depression, as indicated by at least one of the following:

Apgar score less than 5 at 10 minutes of age, need for resuscitation at 10 minutes of age, pH less than 7.00 in a cord blood gas, or in a neonate blood gas obtained at a time less than 60 minutes of age, and/or base deficit ≥15 mmol/L, or ≥12 mmol/L or ≥16 mmol/L in a cord (arterial or venous) gas, or in an infant gas (arterial or venous) obtained at a time less than 60 minutes of age.

9. The method of claim 1, wherein the subject has a gestational age at birth of at least 36 weeks.

10. The method of claim 1, wherein the subject weighs at least 1800 grams at birth.

11. The method of claim 1, wherein the NGF is administered to the subject for the first time within 24 hours after birth.

12. The method of claim 1, wherein the NGF is administered to the subject for the first time between 1 month and 4 months after birth.

13. The method of claim 1, wherein the NGF is administered to the subject with continuous administration schedule, with two or more cycles of periods of treatment, wherein each cycle of the two or more cycles of periods is one week long.

14. The method of claim 1, wherein the NGF is administered to the subject with intermittent administration schedule, with two or more cycles of periods of treatment, wherein each cycle of the two or more cycles of periods is one week long alternated by wash-out periods.

15. The method of claim 1, wherein the NGF is administered to the subject with an intermittent administration schedule, with two or more cycles of periods of treatment alternated by wash-out periods.

16. The method of claim 1, wherein the total dose of the NGF that is administered to the subject is between 25 µg/kg and 400 µg/kg.

17. The method of claim 1, wherein the dose per cycle of the NGF that is administered to the subject is between 15 µg/kg and 20 µg/kg.

18. The method of claim 1, wherein the daily dose of the NGF that is administered to the subject is between 2 µg/kg and 3 µg/kg.

19. The method of claim 1, wherein the subject undergoes therapeutic hypothermia treatment within the first six hours after birth.

20. The method of claim 1, wherein the NGF is formulated as a pharmaceutical composition, wherein the pharmaceutical composition comprises at least one pharmaceutically acceptable excipient.

21. The method of claim 20, wherein the pharmaceutical composition comprises sodium chloride, phosphate buffer, and water.

22. A method of reducing likelihood or reducing severity of occurrence of cerebral palsy associated with neonatal hypoxic-ischemic encephalopathy in a human subject in need thereof, the method comprising administering a therapeutically effective amount of nerve growth factor (NGF) intranasally to the subject only subsequent to a neonatal hypoxic-ischemic event, wherein the NGF comprises SEQ ID NO:1, wherein the reducing likelihood or reducing severity of occurrence of cerebral palsy associated with neonatal hypoxic-ischemic encephalopathy is compared to a subject who has not received NGF.

23. The method of claim 22, wherein the subject who has not received NGF has been diagnosed with neonatal hypoxic-ischemic encephalopathy.

* * * * *